US010760943B2

(12) United States Patent
Hu et al.

(10) Patent No.: US 10,760,943 B2
(45) Date of Patent: Sep. 1, 2020

(54) MEASUREMENT METHOD, MEASUREMENT DEVICE, AND PROGRAM FOR MEASURING A VOLUME OF A DRUG FILLED IN A NEEDLE-SHAPED RECESS

(71) Applicant: FUJIFILM Corporation, Tokyo (JP)

(72) Inventors: Yi Hu, Ashigarakami-gun (JP); Takashi Murooka, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 525 days.

(21) Appl. No.: 15/697,676

(22) Filed: Sep. 7, 2017

(65) Prior Publication Data
US 2018/0058903 A1  Mar. 1, 2018

Related U.S. Application Data

(63) Continuation of application No. PCT/JP2016/055380, filed on Feb. 24, 2016.

(30) Foreign Application Priority Data

Mar. 10, 2015 (JP) .................................. 2015-047620
Dec. 4, 2015 (JP) .................................. 2015-237380

(51) Int. Cl.
*G01F 22/00* (2006.01)
*G01F 23/292* (2006.01)
(Continued)

(52) U.S. Cl.
CPC ........... *G01F 23/292* (2013.01); *A61M 37/00* (2013.01); *A61M 37/0015* (2013.01);
(Continued)

(58) Field of Classification Search
CPC ........ A61M 5/1782; A61M 2205/3306; A61M 37/0015; G01B 11/00; G01B 11/24;
(Continued)

(56) References Cited

U.S. PATENT DOCUMENTS 7,323,705 B2    1/2008  Haga et al.
10,345,098 B2 *  7/2019  Hu ..................... G01B 11/2441
(Continued)

FOREIGN PATENT DOCUMENTS

JP     11-132830 A    5/1999
JP   2002-323503 A   11/2002
(Continued)

OTHER PUBLICATIONS

Communication dated Feb. 20, 2018, from Japanese Patent Office in counterpart application No. 2015-237380.
(Continued)

*Primary Examiner* — Que Tan Le
(74) *Attorney, Agent, or Firm* — Sughrue Mion, PLLC

(57) ABSTRACT

A measurement method measuring a volume of a drug in each needle-shaped recess of a mold includes: acquiring a reference surface height that is a height between a reference surface determined in advance with respect to a first surface on the side on which a drug is filled in the mold or a second surface opposite to the first surface, and the second surface; acquiring a first detection result by detecting a measurement wave emitted from a drug surface according to incidence of the measurement wave on the drug in the needle-shaped recess; detecting a first height between the reference surface and the drug surface; detecting a second height from the second surface to the drug surface based on the reference surface height and the first height; and calculating a volume of the drug based on the second height and a known shape of the needle-shaped recess.

22 Claims, 23 Drawing Sheets

(51) Int. Cl.
  *A61M 37/00* (2006.01)
  *G01B 11/00* (2006.01)
  *G01B 11/24* (2006.01)
  *G01F 23/00* (2006.01)

(52) U.S. Cl.
  CPC .............. *G01B 11/00* (2013.01); *G01B 11/24* (2013.01); *G01F 22/00* (2013.01); *G01F 23/2928* (2013.01); *A61M 2037/0023* (2013.01); *A61M 2037/0053* (2013.01); *A61M 2205/3306* (2013.01); *A61M 2205/3382* (2013.01); *A61M 2207/10* (2013.01); *G01F 23/0061* (2013.01)

(58) Field of Classification Search
  CPC ..... G01B 11/22; G01B 11/2441; G01F 22/00; G01F 17/00; G01F 25/0004; G01F 23/0061; G01F 23/292; G01F 23/2928
  USPC .......................................... 250/573–577, 221
  See application file for complete search history.

(56) References Cited

U.S. PATENT DOCUMENTS

| | | |
|---|---|---|
| 2002/0121139 A1 | 9/2002 | Purpura et al. |
| 2003/0037611 A1 | 2/2003 | Purpura et al. |
| 2004/0101440 A1 | 5/2004 | Ishizawa et al. |
| 2006/0178578 A1 | 8/2006 | Tribble et al. |
| 2008/0304082 A1 | 12/2008 | Gotz et al. |

FOREIGN PATENT DOCUMENTS

| | | |
|---|---|---|
| JP | 2008-224673 A | 9/2008 |
| JP | 2011-224332 A | 11/2011 |
| JP | 2012-254952 A | 12/2012 |
| JP | 2013-162982 A | 8/2013 |

OTHER PUBLICATIONS

Anonymous. "Bioassay", Wikipedia, Jan. 27, 2015, XP055449980, Retrieved from the Internet: URL: https://en.wikipedia.org/w/index.php?title=Bioassay&oldid=644423738 [retrieved on Feb. 9, 20189], total 4 pages.

Communication dated Mar. 8, 2018, from European Patent Office in counterpart application No. 16761484.1.

International Search Report dated May 24, 2016 issued by the International Searching Authority in international application No. PCT/JP2016/055380.

International Preliminary Report on Patentability with the translation of Written Opinion dated Sep. 12, 2017 issued by the Internal Bureau in international application No. PCT/JP2016/055380.

Communication dated Aug. 2, 2018 from the Japanese Patent Office in counterpart application No. 2015-237380.

Communication dated Mar. 10, 2020,from the European Patent Office in application No. 16761484.1.

\* cited by examiner

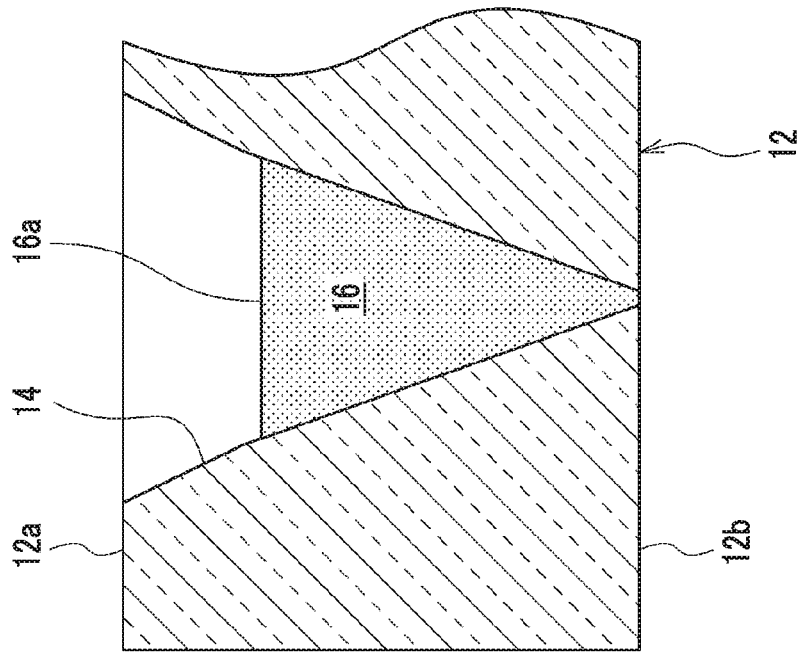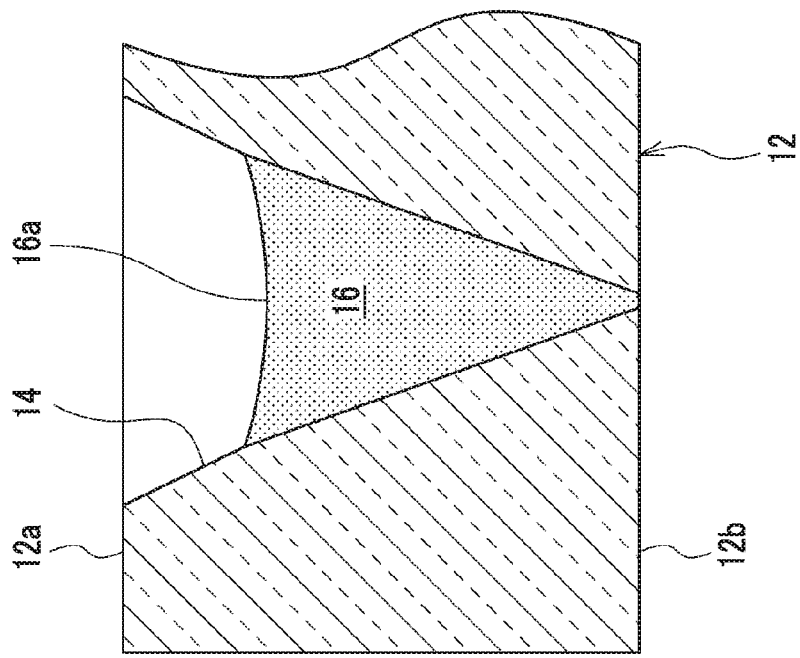

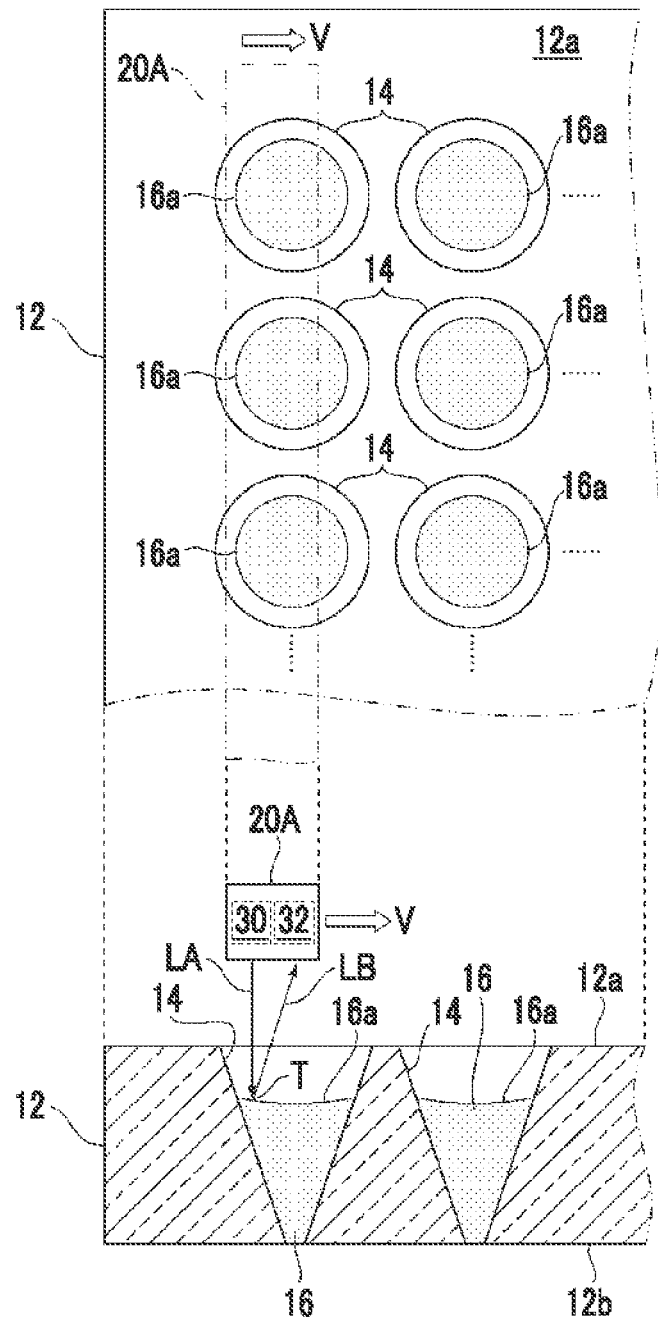

MEASUREMENT METHOD, MEASUREMENT DEVICE, AND PROGRAM FOR MEASURING A VOLUME OF A DRUG FILLED IN A NEEDLE-SHAPED RECESS

CROSS-REFERENCE TO RELATED APPLICATIONS

This application is a Continuation of PCT International Application No. PCT/JP2016/055380 filed on Feb. 24, 2016, which claims priorities under 35 U.S.C. §119(a) to Japanese Patent Application No. 2015-047620 filed on Mar. 10, 2015 and Japanese Patent Application No. 2015-237380 filed on Dec. 4, 2015. Each of the above applications is hereby expressly incorporated by reference, in their entirety, into the present application.

BACKGROUND OF THE INVENTION

1. Field of the Invention

The present invention relates to a measurement method, a measurement device, and a program for measuring a volume of a drug filled in a needle-shaped recess of a mold that forms a microneedle.

2. Description of the Related Art

In recent years, a micro-needle array (hereinafter abbreviated as MNA) is known as a novel dosage form capable of administering a drug such as insulin, vaccines, and human Growth Hormone (hGH) into the skin without pain. In the MNA, biodegradable micro-needles containing a drug are arranged in an array form. By affixing this MNA to a skin, each micro-needle can pierce the skin, the micro-needle can be absorbed into the skin, and the drug contained in each micro-needle can be administered into the skin.

As a method of manufacturing such an MNA, a method of filling and drying a drug in a solution state (a drug solution in which a drug or the like is dissolved in water) in each needle-shaped recess of a mold having a large number of needle-shaped recesses that are inverted types of MNA to form the MNA, and then, peeling the MNA from the mold is known (see JP2013-162982A and JP2012-254952A). When the MNA is manufactured, it is necessary to strictly manage the amount of the drug to be administered into the skin from the MNA. Therefore, in the MNA manufacturing process, measurement of the amount of the drug contained in the MNA is performed.

In the method of manufacturing an MNA described in JP2011-224332A, the amount of the drug contained in the MNA is measured by dissolving MNA in water. However, in the method described in JP2011-224332A, there is a problem in that a produced MNA is destructed because destructive measurement is required.

Therefore, in order to quantify the amount of a drug contained in the MNA, measurement of a volume (capacity) of the drug filled in each needle-shaped recess of the mold is performed. For example, a method of measuring a weight of a mold before filling of a drug and a weight of the mold after filling of the drug with a high-precision electronic balance and measuring a volume of the drug filled in each needle-shaped recess on the basis of a weight difference before and after filling and a density of the drug is known. According to the method of measuring the volume with this high-precision electronic balance, it is possible to perform non-destructive measurement of the volume of the drug filled in each needle-shaped recess of the mold.

SUMMARY OF THE INVENTION

However, in a case where measurement using the high-precision balance is performed, it is necessary to prepare a high-precision electronic balance having both a measurement range and resolution suitable for measurement. For example, a case where a weight of the mold is 800 mg and the mold is filled with 2 mg of a drug will be described by way of example. In this case, if an allowable range of a variation in the volume of 2 mg is ±3% of 2 mg, this allowable range is ±0.06 mg. Thus, it is necessary for the high-precision electronic balance to have a resolution of 0.01 mg. However, since the weight of the mold is 800 mg, which is much larger than the weight of the drug filled in the needle-shaped recess by about 400 times, it is necessary to secure 800 mg as a measurement range of the high-precision electronic balance. Therefore, it is actually difficult to prepare a high-performance electronic balance with the measurement range (800 mg) and the resolution (0.01 mg), and the volume of the drug filled in the needle-shaped recess cannot be measured with high precision on the basis of a weight difference before and after filling.

Further, in the measurement using the high-precision electronic balance as described above, the volume of the drug of each needle-shaped recess of the mold cannot be individually measured. As a result, a variation in the volume of the drug of each needle-shaped recess cannot be measured. Therefore, development of a technology capable of nondestructively measuring the volume of a drug of each needle-shaped recess of the mold with high precision is desired. Further, in this case, since MNAs of a plurality of kinds of drugs such as insulin and vaccines are generally manufactured while switching the MNAs in an MNA manufacturing process, development of a measurement technology that does not depend on a kind of drug is desired.

JP2012-254952A described above discloses a method of coloring each micro-needle of the MNA with blue, observing the blue micro-needle peeled from the mold with a video microscope, and measuring a length of a colored part. Since a shape of each needle-shaped recess of the mold is known, an individual volume (capacity) of the micro-needle in each needle-shaped recess is obtained on the basis of a measurement result of the length of the micro-needle in each needle-shaped recess. However, in this method, the micro-needle after drying is a measurement target. Accordingly, the method can be carried out irrespective of a kind of drug, but cannot be applied to the measurement of the volume of the drug filled in the individual needle-shaped recess of the mold.

The present invention has been made in view of the above circumstances, and an object of the present invention is to provide a measurement method, a measurement device, and a program capable of non-destructively measuring a volume of a drug in each needle-shaped recess of a mold with high accuracy.

A measurement method for achieving the object of the present invention is a measurement method of measuring a volume of a drug filled in a needle-shaped recess of a mold in which a plurality of needle-shaped recesses that are inverted types of a micro-needle are formed, the measurement method comprising: a reference surface height acquisition step of acquiring a reference surface height that is a height between a reference surface determined in advance with respect to a first surface on the side on which the drug is filled in the mold or a second surface opposite to the first surface, and the second surface; a detection result acquisition step of acquiring a first detection result obtained by detecting, for each needle-shaped recess, a measurement wave emitted from a drug surface that is a surface of the drug according to incidence of the measurement wave on the drug in the needle-shaped recess; a first height detection step of detecting, for each needle-shaped recess, a first height between the reference surface and the drug surface on the basis of the first detection result acquired the detection result acquisition step; a second height detection step of detecting, for each needle-shaped recess, a second height from the second surface to the drug surface, from the reference surface height acquired in the reference surface height acquisition step and the first height of each needle-shaped recess detected in the first height detection step; and a volume calculation step of calculating, for each needle-shaped recess, the volume of the drug in the needle-shaped recess on the basis of the second height of each needle-shaped recess detected in the second height detection step and a known shape of the needle-shaped recess. The reference surface determined in advance with respect to the first surface or the second surface opposite to the first surface includes a reference surface parallel (including substantially parallel) to the first surface or the second surface, and "parallel to the first surface or the second surface" also includes "parallel to both of the first surface and the second surface".

According to this measurement method, it is possible to measure the volume of the drug in each needle-shaped recess on the basis of the first detection result obtained by detecting the measurement wave emitted from the drug surface in each needle-shaped recess of the mold due to the incidence of the measurement wave and a reference surface height that is a height between the predetermined reference surface and the second surface.

In the measurement method according to another aspect of the present invention, the volume calculation step includes calculating a total volume of the drug filled in the mold from the volume of the drug of each needle-shaped recess. Thus, it is possible to measure the total volume of the drug filled in the mold.

In the measurement method according to still another aspect of the present invention, the detection result acquisition step includes acquiring, for each needle-shaped recess, the first detection result obtained by detecting the measurement wave emitted from the plurality of positions according to the incidence of the measurement wave on the plurality of positions of the drug surface, the first height detection step includes detecting, for each needle-shaped recess, the first height from the plurality of positions to the reference surface on the basis of the first detection result of each needle-shaped recess acquired in the detection result acquisition step, the second height detection step includes detecting, for each needle-shaped recess, the second height from the second surface to each of the plurality of positions from the reference surface height and the first height of the plurality of positions of each needle-shaped recess detected in the first height detection step, and the volume calculation step includes calculating the volume of the drug in the needle-shaped recess for each needle-shaped recess on the basis of the second height of the plurality of positions of each needle-shaped recess detected in the second height detection step and the known shape of the needle-shaped recess. Thus, since the shape of the drug surface in the needle-shaped recess is reflected in calculation of the volume of the drug, it is possible to more accurately calculate the volume of the drug 16 of each needle-shaped recess.

In the measurement method according to another aspect of the present invention, the detection result acquisition step includes acquiring the first detection result obtained by a plurality of detection units detecting the measurement wave emitted in different directions from the plurality of positions according to incidence of the measurement wave on the plurality of positions of each needle-shaped recess from the plurality of incidence units, the first height detection step includes performing the detection of the first height of the plurality of positions for each needle-shaped recess in each detection unit on the basis of the first detection result of each detection unit acquired in the detection result acquisition step, the second height detection step includes performing the detection of the second height of the plurality of positions for each needle-shaped recess in each detection unit, on the basis of the first height of the plurality of positions of each detection unit detected in the first height detection step, and the reference surface height, and the volume calculation step includes integrating, for each the needle-shaped recess, the second height of the plurality of positions of each detection unit detected in the second height detection step, and calculating the volume of the drug in the needle-shaped recess for each needle-shaped recess on the basis of the second integrated height of the plurality of positions of each needle-shaped recess and the known shape of the needle-shaped recess. Accordingly, since it is possible to reliably detect the first height and the second height of a plurality of positions on the drug surface of each needle-shaped recess, it is possible to obtain the volume of the drug in each needle-shaped recess more accurately.

In the method according to still another aspect of the present invention, the detection result acquisition step includes performing incidence of the measurement wave at an incidence angle determined in advance for every plurality of positions on the plurality of positions from the incidence unit while relatively moving the mold and the incidence unit that causes the measurement wave to be incident on the drug surface in a direction parallel to the first surface, and detecting the measurement wave emitted from each of the plurality of positions according to the incidence of the measurement wave using the detection unit to acquire the first detection result. Accordingly, since it is possible to reliably detect the first height and the second height of the plurality of positions on the drug surface for each needle-shaped recess, it is possible to obtain the volume of the drug in each needle-shaped recess more accurately.

In the method according to still another aspect of the present invention, the detection result acquisition step includes performing incidence of the measurement wave on the plurality of positions from the incidence unit while relatively moving the mold and the incidence unit that causes the measurement wave to be incident on the drug surface in a direction parallel to the first surface, and detecting the measurement wave emitted in a direction determined in advance for every plurality of positions from the plurality of positions according to the incidence of the measurement wave using the detection unit to acquire the first detection result. Accordingly, since it is possible to reliably detect the first height and the second height of the plurality of positions on the drug surface for each needle-shaped recess, it is possible to obtain the volume of the drug in each needle-shaped recess more accurately.

In the method according to still another aspect of the present invention, the detection result acquisition step includes performing scan for causing the measurement wave to be incident on the plurality of positions from the incidence unit a plurality of times while relatively moving the mold and the incidence unit that causes the measurement wave to be incident on the drug surface in a direction parallel to the first surface, and detecting, for each scan, the measurement wave emitted in a different direction from the plurality of positions for each scan using the detection unit to acquire the first detection result, the first height detection step includes performing, for each scan, detection of the first height of the plurality of positions of each needle-shaped recess on the basis of the first detection result for each scan acquired in the detection result acquisition step, the second height detection step includes performing, for each scan, the detection of the second height of the plurality of positions for each needle-shaped recess on the basis of the first height of the plurality of positions for each scan detected in the first height detection step, and the reference surface height, and the volume calculation step includes integrating, for each the needle-shaped recess, the second height of the plurality of positions of each scan detected in the second height detection step, and calculating the volume of the drug in the needle-shaped recess for each needle-shaped recess on the basis of the second integrated height of the plurality of positions of each needle-shaped recess and the known shape of the needle-shaped recess. Accordingly, since it is possible to reliably detect the first height and the second height of the plurality of positions on the drug surface for each needle-shaped recess, it is possible to obtain the volume of the drug in each needle-shaped recess more accurately.

In the measurement method according to still another aspect of the present invention, the detection result acquisition step starts within a predetermined time after the drug is filled in the needle-shaped recesses of the mold or at a certain time within a predetermined time. Accordingly, the measurement can be started when the state of the drug filled in each needle-shaped recess does not change. Further, by starting the measurement at a certain time within a predetermined time, the measurement of the volume of the drug in the needle-shaped recess can always be performed under the same condition.

In the measurement method according to still another embodiment of the present invention, the volume of the drug decreases over time due to evaporation of water contained in the drug, the measurement method further comprises: an elapsed time acquisition step of acquiring an elapsed time until the detection result acquisition step starts after the drug is filled in the needle-shaped recess of the mold; and a correction value acquisition step of acquiring a correction value for correcting a decrease over time in the volume of the drug filled in the needle-shaped recess, and the volume calculation step includes correcting the volume of the drug in the needle-shaped recess with the correction value acquired in the correction value acquisition step on the basis of the elapsed time acquired in the elapsed time acquisition step, and calculating the amount of filling of the drug filled in the needle-shaped recess for each needle-shaped recess. Accordingly, since the amount of filling of the drug filled in each needle-shaped recess can be measured, this measurement result can be fed back to a filling device that fills a drug in each needle-shaped recess of the mold. As a result, it is possible to appropriately adjust the amount of filling of the drug to each needle-shaped recess in the filling device.

A measurement method according to still another aspect of the present invention further comprises: a first incidence step of causing the measurement wave to be incident on the drug surface in each needle-shaped recess; and a first detection step of detecting, for each needle-shaped recess, the measurement wave emitted from the drug surface according to the incidence of the measurement wave in the first incidence step, and the detection result acquisition step includes acquiring the first detection result of the measurement wave detected in the first detection step. Thus, it is possible to acquire the first detection result that is used for detection of the first height.

In the measurement method according to still another aspect of the present invention, the reference surface is the first surface, the reference surface height is a thickness of the mold, and the reference surface height acquisition step includes acquiring the reference surface height from the storage unit that stores the reference surface height in advance. Accordingly, it is possible to simply acquire the reference surface height.

In the measurement method according to still another aspect of the present invention, the reference surface is the first surface, the reference surface height is a thickness of the mold, the reference surface height acquisition step includes acquiring a second detection result obtained by detecting the measurement wave emitted from the first surface and the second surface according to incidence of the measurement wave on the non-formation region of the needle-shaped recess included in the mold, and acquiring the thickness of the mold as the reference surface height on the basis of the second detection result. Accordingly, the second height can be detected on the basis of the actual measurement value of the reference surface height (a thickness of the mold). As a result, even when there is a manufacturing error in the thickness of the mold, this manufacturing error can be reflected in the detection of the second height. Therefore, it is possible to obtain the volume of the drug in each needle-shaped recess more accurately.

The measurement method according to another aspect of the present invention further comprises: a second incidence step of causes the measurement wave to be incident on the non-formation region of the mold; and a second detection step of detecting the measurement wave emitted from the first surface and the second surface of the non-formation region according to the incidence of the measurement wave in the second incidence step, wherein the reference surface height acquisition step includes acquiring the second detection result of the measurement wave detected in the second detection step. Accordingly, the second height can be detected on the basis of the actual measurement value of the reference surface height (the thickness of the mold).

In the measurement method according to still another aspect of the present invention, the second incidence step includes causing the measurement wave to be incident on the first surface of the non-formation region, and the second detection step includes detecting the measurement wave emitted from the first surface due to reflection at the first surface according to the incidence of the measurement wave in the second incidence step, and the measurement wave incident on the mold from the first surface and emitted from the second surface due to reflection at the second surface of the non-formation region. Accordingly, it is possible to acquire the second detection result that is used for acquisition of the reference surface height (the thickness of the mold).

In the measurement method according to still another aspect of the present invention, the reference surface is a plane that is at the same height as that of the detection unit that detects the measurement wave emitted from the drug surface. By setting the reference surface as a plane that is the same height as that of the detection unit, it is possible to detect the first height through one measurement, unlike a case where the reference surface is the first plane.

The measurement method according to still another embodiment of the present invention further comprises adding a dye to the drug that is filled in the needle-shaped recess. Accordingly, since the surface of the drug in the needle-shaped recess can be easily recognized, it is possible to easily perform incidence of the measurement wave on the surface of the drug.

The measurement method according to still another aspect of the present invention further comprises performing hydrophilic treatment on the first surface before filling of the drug in the needle-shaped recess. Accordingly, since the drug surface in the needle-shaped recess can be planarized, an error between the detection result of the second height described above and an actual height in the entire surface of the drug is reduced. Thus, it is possible to measure the volume of the drug in each needle-shaped recess with higher accuracy.

A measurement device for achieving the object of the present invention is a measurement device that measures a volume of a drug filled in a needle-shaped recess of a mold in which a plurality of needle-shaped recesses that are inverted types of a micro-needle are formed, the measurement device comprising: a reference surface height acquisition unit that acquires a reference surface height that is a height between a reference surface determined in advance with respect to a first surface on the side on which the drug is filled in the mold or a second surface opposite to the first surface, and the second surface; a detection result acquisition unit that acquires a first detection result obtained by detecting, for each needle-shaped recess, a measurement wave emitted from a drug surface that is a surface of the drug according to incidence of the measurement wave on the drug in the needle-shaped recess; a first height detection unit that detects, for each needle-shaped recess, a first height between the reference surface and the drug surface on the basis of the first detection result acquired by the detection result acquisition unit; a second height detection unit that detects, for each needle-shaped recess, a second height from the second surface to the drug surface from the reference surface height acquired by the reference surface height acquisition unit and the first height of each needle-shaped recess detected by the first height detection unit; and a volume calculation unit that calculates, for each needle-shaped recess, the volume of the drug in the needle-shaped recess on the basis of the second height of each needle-shaped recess detected by the second height detection unit and a known shape of the needle-shaped recess.

The measurement device according to still another aspect of the present invention further comprises a first incidence unit that causes the measurement wave to be incident on the drug in the needle-shaped recess, for each needle-shaped recess; and a first detection unit that detects, for each needle-shaped recess, the measurement wave emitted from the drug surface according to the incidence of the measurement wave by the first incidence unit, wherein the detection result acquisition unit acquires the first detection result of the measurement wave detected by the first detection unit.

In the measurement device according to still another aspect of the present invention, the reference surface is the first surface, the reference surface height is a thickness of the mold, the measurement device includes a second incidence unit that causes the measurement wave to be incident on a non-formation region of the needle-shaped recess included in the mold; and a second detection unit that detects the measurement wave emitted from the first surface and the second surface of the non-formation region according to the incidence of the measurement wave by the second incidence unit, and the reference surface height acquisition unit acquires the second detection result of the measurement wave detected by the second detection unit, and acquires the thickness of the mold as the reference surface height on the basis of the second detection result.

In the measurement device according to still another aspect of the present invention, the reference surface height acquisition unit acquires the reference surface height from the storage unit that stores the reference surface height in advance.

A program for achieving the object of the present invention is a program that causes a computer to function as means for measuring a volume of a drug filled in a needle-shaped recess of a mold in which a plurality of needle-shaped recesses that are inverted types of a micro-needle are formed, the program causing the computer to function as: a reference surface height acquisition unit that acquires a reference surface height that is a height between a reference surface determined in advance with respect to a first surface on the side on which the drug is filled in the mold or a second surface opposite to the first surface, and the second surface; a detection result acquisition unit that acquires a first detection result obtained by detecting, for each needle-shaped recess, a measurement wave emitted from a drug surface that is a surface of the drug according to incidence of the measurement wave on the drug in the needle-shaped recess; a first height detection unit that detects, for each needle-shaped recess, a first height between the reference surface and the drug surface on the basis of the first detection result acquired by the detection result acquisition unit; a second height detection unit that detects, for each needle-shaped recess, a second height from the second surface to the drug surface from the reference surface height acquired by the reference surface height acquisition unit and the first height of each needle-shaped recess detected by the first height detection unit; and a volume calculation unit that calculates, for each needle-shaped recess, the volume of the drug in the needle-shaped recess on the basis of the second height of each needle-shaped recess detected by the second height detection unit and a known shape of the needle-shaped recess. A computer-readable non-transitory tangible medium having this program recorded thereon is also included in aspects of the present invention.

In the measurement method, the measurement device, and the program of the present invention, it is possible to non-destructively measure the volume of the drug in each needle-shaped recess of the mold with high accuracy.

BRIEF DESCRIPTION OF THE DRAWINGS

FIG. 12A is a cross-sectional view of the mold in which hydrophilic treatment is not performed on a first surface, and FIG. 12B is a cross-sectional view of the mold in which the hydrophilic treatment is performed on the first surface.

FIG. 13A is a top view of the laser displacement meter of the measurement device of a second embodiment, and FIG. 13B is a side view of the laser displacement meter.

DESCRIPTION OF THE PREFERRED EMBODIMENTS

Overall Configuration of Measurement Device of First Embodiment

Figure 1:
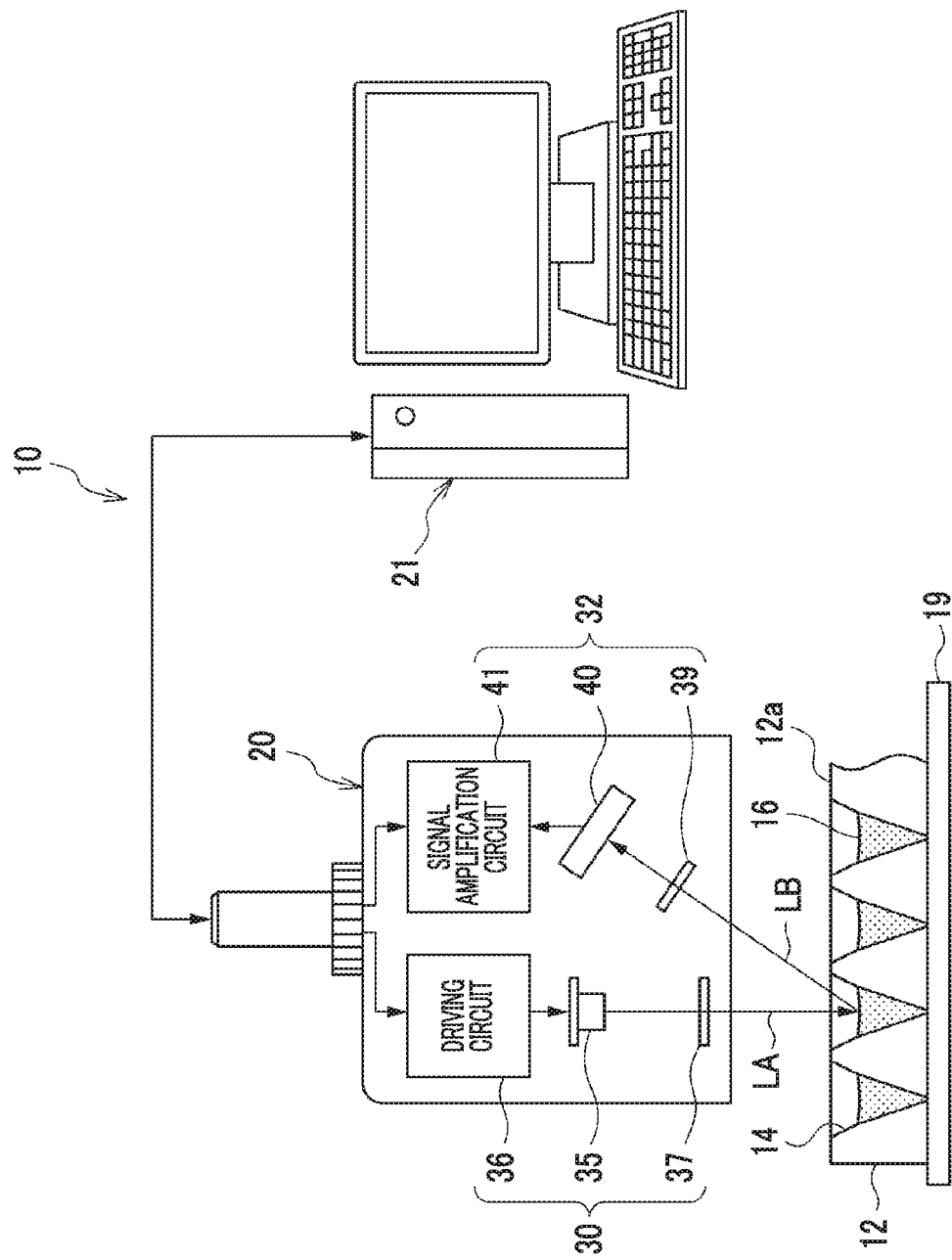
FIG. 1 is a schematic diagram of a measurement device according to a first embodiment in which a volume of a drug filled in each needle-shaped recess of a mold is measured.

FIG. 1 is a schematic diagram of a measurement device 10 according to a first embodiment of a measurement method and a measurement device of the present invention. This measurement device 10 measures a volume of the drug 16 filled in each needle-shaped recess 14 of the mold 12. As illustrated in FIG. 1, the measurement device 10 mainly includes a flat plate-shaped stage 19 that supports the mold 12, a laser displacement meter (also referred to as a laser displacement sensor or a laser distance sensor) 20, and a device body 21.

Figure 2:
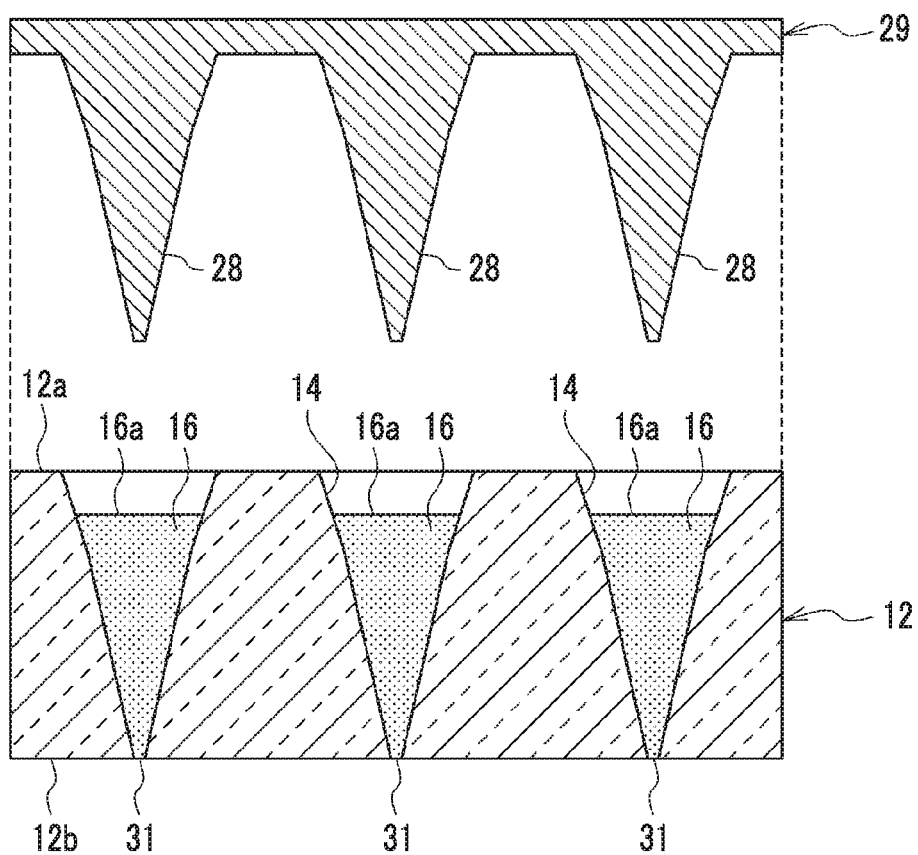
FIG. 2 is a cross-sectional view of the mold.

FIG. 2 is a cross-sectional view of the mold 12. As illustrated in FIG. 2, the mold 12 is a flat plate-shaped mold that is used for manufacture of an MNA 29 in which micro-needles 28 are arranged in an array form. In this embodiment, this mold 12 is formed of, for example, silicon rubber and has optical transmittance. Here, the optical transmittance is a concept including transparent and semi-transparent, and more particularly, is a property of transmitting at least a part of laser light LA (a measurement wave) that is emitted from a laser displacement meter 20 to be described below. A plurality of needle-shaped recesses 14 that are an inverted type of micro-needles 28 are formed in an array form in the mold 12.

A drug 16 in a solution state (also referred to as a drug solution) is filled in the needle-shaped recess 14 from the first surface 12a (an upper surface in FIG. 2) of the mold 12. In the drug 16 in a solution state, water occupies about 80%, a proportion of the drug 16 is several %, and the remainder is a hydroxyethyl starch (HES) solution or the like. Reference sign "16a" in FIG. 2 is a drug surface indicating a surface (liquid surface) of the drug 16 filled in the needle-shaped recess 14.

The needle-shaped recesses 14 have a conical shape that gradually tapers from a first surface 12a to a second surface 12b opposite to the first surface 12a, corresponding to a shape of the micro-needles 28. Therefore, a wall surface of the needle-shaped recess 14 is an inclined surface. In this embodiment, the needle-shaped recess is formed so that an inclination angle of an opening adjacent portion on the first surface 12a side among wall surfaces of the needle-shaped recesses 14 is smaller than an inclination angle of other portions.

A communication hole 31 communicating with each needle-shaped recess 14 is formed for each needle-shaped recess 14 in the second surface 12b of the mold 12. A diameter of the communication hole 31 is, for example, 30 µm. The mold 12 is set on the stage 19 in a state in which the first surface 12a is directed to top in FIG. 2 and the second surface 12b is directed to bottom in FIG. 2 after the drug 16 is filled in the needle-shaped recesses 14.

Figure 3:
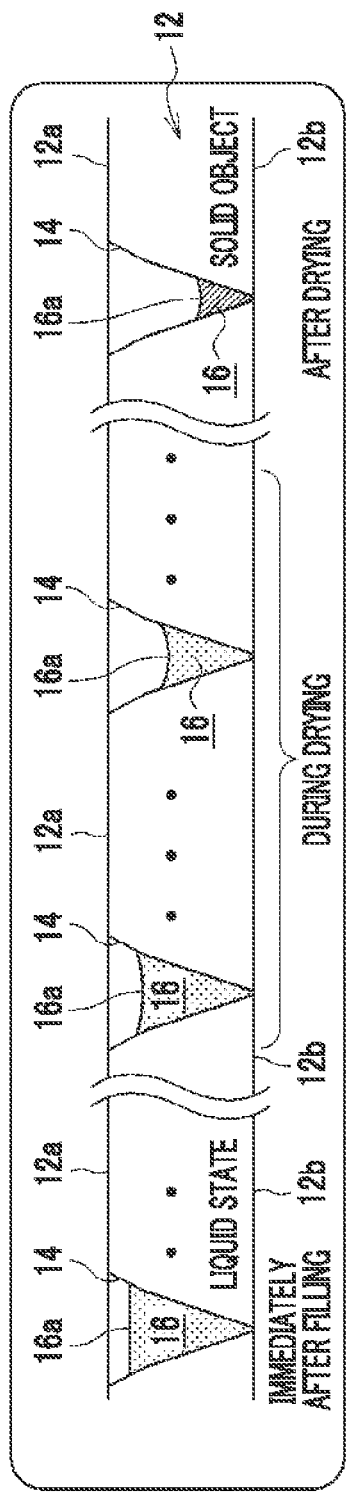
FIGS. 3A through 3C are illustrative views illustrating a state of a drug filled in each needle-shaped recess of the mold.

FIGS. 3A through 3C show an illustrative diagram illustrating a state of the drug 16 filled in each needle-shaped recess 14 of the mold 12. Here, FIG. 3A illustrates a state immediately after the drug 16 in a solution state is filled in the needle-shaped recess 14, FIG. 3B illustrates a state in which the mold 12 is being dried, and FIG. 3C is a state after the mold 12 is dried.

As illustrated in FIG. 3A to 3C, the mold 12 is dried after the drug 16 in a solution state is filled in each needle-shaped recesses 14, water evaporates from the drug 16 in each needle-shaped recess 14 over time, and the drug 16 in a solution state is eventually solidified as a solid object. Accordingly, the micro-needle 28 that is a crystal of the drug 16 is formed in each needle-shaped recess 14, and the MNA 29 is formed on the first surface 12a of the mold 12. This MNA 29 is peeled from the mold 12.

The measurement device 10 measures the volume of the drug 16 (containing water) in a solution state in each needle-shaped recess 14 if a measurement time is before solidification of the drug 16, and measures the volume of the drug 16 in a solid state in each needle-shaped recess 14 if the measurement time is after the solidification of the drug 16. In a case where the measurement is performed during drying of the mold 12 illustrated in FIG. 3B, that is, in a case where the measurement of the volume of the drug 16 in a solution state is performed, it is preferable for the measurement to be started within a predetermined time after the drug 16 is filled in the needle-shaped recesses 14 of the mold 12 or at a certain time within the predetermined time. Here, "within a predetermined time" is in a time in which there is no great change in the state of the drug 16 in a measurement time. Since this time is changed due to manufacturing conditions of the MNA 29 (a kind of drug 16, a shape of the needle-shaped recess 14, temperature at the time of drying, or the like), the time is determined by performing an experiment, simulation, or the like for each manufacturing condition. For example, "within a predetermined time" in this embodiment is in 5 minutes. Further, if the measurement starts at a certain time within a predetermined time, the measurement of the volume of the drug 16 in the needle-shaped recess 14 can be always performed under the same conditions in a case where the water evaporates from the drug 16.

Referring back to FIG. 1, the stage 19 movably supports the mold 12 in a parallel direction parallel (including substantially parallel) to the first surface 12*a* thereof (hereinafter simply referred to as a parallel direction) and a height direction perpendicular to the first surface 12*a* (hereinafter simply referred to as a height direction). A position adjustment mechanism (not illustrated) for adjusting positions in the parallel direction and the height direction of the mold 12 is provided on the stage 19. By an operator operating the position adjustment mechanism, it is possible to adjust a relative position between the mold 12 and the laser displacement meter 20 to be described below. Although the position adjustment in the position adjustment mechanism can be both manual adjustment and automatic adjustment, a case where the manual adjustment is performed will be described in this embodiment. Further, a method of adjusting the relative position between the mold 12 and the laser displacement meter 20 is not particularly limited, and the laser displacement meter 20 may be moved.

The laser displacement meter 20 is arranged at a position facing the first surface 12*a* of the mold 12 supported on the stage 19, that is, over the mold 12 in FIG. 1. As this laser displacement meter 20, for example, a light diffusion, reflection, and reception type charge coupled device (CCD) laser displacement meter adopting a triangular distance measurement scheme may be used. A complementary metal oxide semiconductor (CMOS) laser displacement meter may be used in place of the CCD laser displacement meter. The light diffusion, reflection, and reception type laser displacement meter 20 causes the laser light LA corresponding to the measurement wave of the present invention to be vertically (vertically herein includes substantially vertically, and the same applies to hereinafter) incident on the mold 12 from the first surface 12*a* of the mold 12, and receives the reflection light LB of the laser light LA diffused and reflected by the mold 12. Here, the laser light LA (reflection light LB) corresponds to the measurement wave of the present invention.

The laser displacement meter 20 includes an incidence unit 30 corresponding to a first incidence unit and a second incidence unit of the present invention, and a detection unit 32 corresponding to a first detection unit and a second detection unit of the present invention.

The incidence unit 30 causes the laser light LA to be vertically incident on the mold 12 from the first surface 12*a* of the mold 12. This incidence unit 30 includes a semiconductor laser light source 35, a driving circuit 36, and a light projecting lens 37.

The semiconductor laser light source 35 emits the laser light LA perpendicular to the first surface 12*a* to the mold 12. The driving circuit 36 drives the semiconductor laser light source 35 to cause laser light LA to be emitted under the control of the device body 21 to be described below. The light projecting lens 37 causes the laser light LA emitted from the semiconductor laser light source 35 to be vertically incident on the mold 12.

The laser light LA vertically incident on the first surface 12*a* of the mold 12 by the incidence unit 30 will be described in detail below and is diffused and reflected by the mold 12. The reflection light LB of the diffused and reflected laser light LA (also referred to as a diffused and reflected component of the reflection light or the diffuse reflection light), that is, the reflection light LB emitted from the mold 12 is incident on the detection unit 32.

The detection unit 32 detects the reflection light LB of the laser light LA. This detection unit 32 includes a light reception lens 39, a CCD type (or a CMOS type) imaging element 40, and a signal amplification circuit 41. The light reception lens 39 causes the reflection light LB diffused and reflected by the mold 12 to be incident on the imaging surface of the imaging element 40.

The imaging element 40 includes an imaging surface in which a plurality of pixels are two-dimensionally arranged, and detects light using each pixel. The above-described reflection light LB is incident as spot light on the imaging surface. Here, the incidence position (spot position) of the reflection light LB on the imaging surface is displaced according to a positional relationship between the laser displacement meter 20 and a reflection point at which the laser light LA is diffused and reflected. Therefore, a relative position of the reflection point of the laser light LA with respect to the reference position of the laser displacement meter 20 or the like can be detected on the basis of the detection result of the light reception amount of each pixel of the imaging element 40. The imaging element 40 outputs a light reception signal indicating the light reception amount of each pixel, as a detection result of the reflection light LB, to the signal amplification circuit 41.

The signal amplification circuit 41 amplifies the light reception signal input from the imaging element 40 and outputs the amplified light reception signal to the device body 21.

Although not illustrated, a camera or an observation optical system for confirming the incidence position of the laser light LA incident on the mold 12 from the laser displacement meter 20 is provided in the measurement device 10. Thus, the operator can cause the laser light LA to be incident on a desired position of the mold 12 by performing position adjustment of the stage 19 using the position adjustment mechanism described above while confirming the incidence position of the laser light LA on the mold 12 using a camera or the like.

Such a laser displacement meter 20 is used to detect the height Ht (see FIG. 4) from the second surface 12*b* of the mold 12 to the drug surface 16*a* in each needle-shaped recess 14. Hereinafter, a method of detecting the height Ht of each needle-shaped recess 14 will be specifically described.

Figure 4:
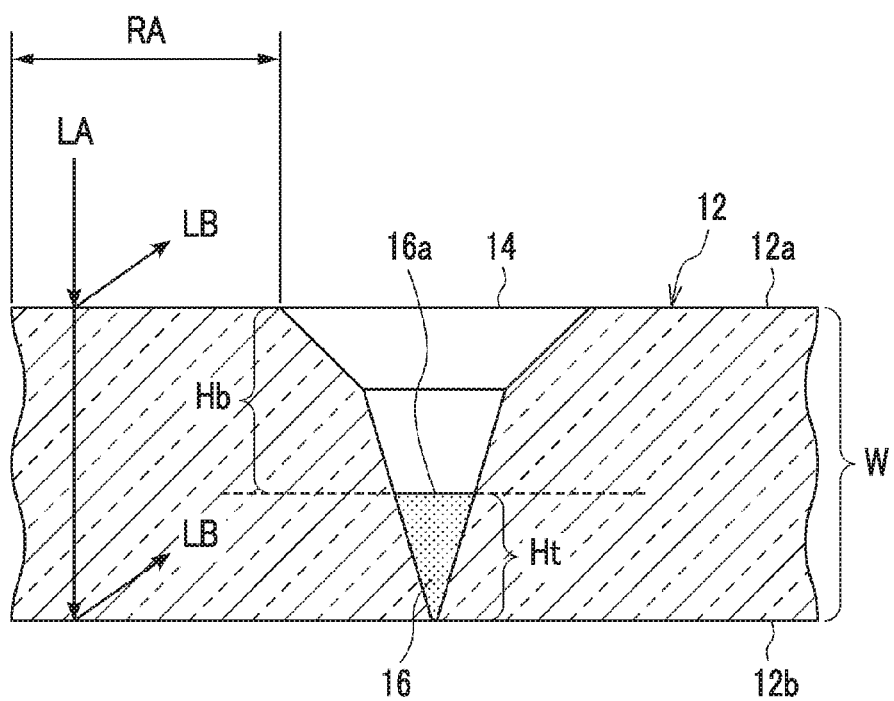
FIG. 4 is an enlarged view of a cross-section of the mold.

FIG. 4 is an enlarged view of a cross-section of the mold 12. As illustrated in FIG. 4, in the measurement device 10, the thickness W of the mold 12 and the height Hb from the drug surface 16a of each needle-shaped recess 14 to the first surface 12a are detected using the laser displacement meter 20, and then, the height Hb of each needle-shaped recess 14 is subtracted from the thickness W. Accordingly, the height Ht is detected for each needle-shaped recess 14. Here, the first surface 12a corresponds to the reference surface of the present invention, the thickness W that is a height between the first surface 12a and the second surface 12b corresponds to the reference surface height of the present invention, the height Hb corresponds to a first height of the present invention, and the height Ht corresponds to a second height of the present invention.

[Detection of Thickness W]

A deviation is likely to occur between a thickness W of the mold 12 and a design value due to causes such as a manufacturing error during manufacture of the mold 12. Therefore, in this embodiment, an actual thickness W of the mold 12 is detected using the laser displacement meter 20.

Figure 5A:
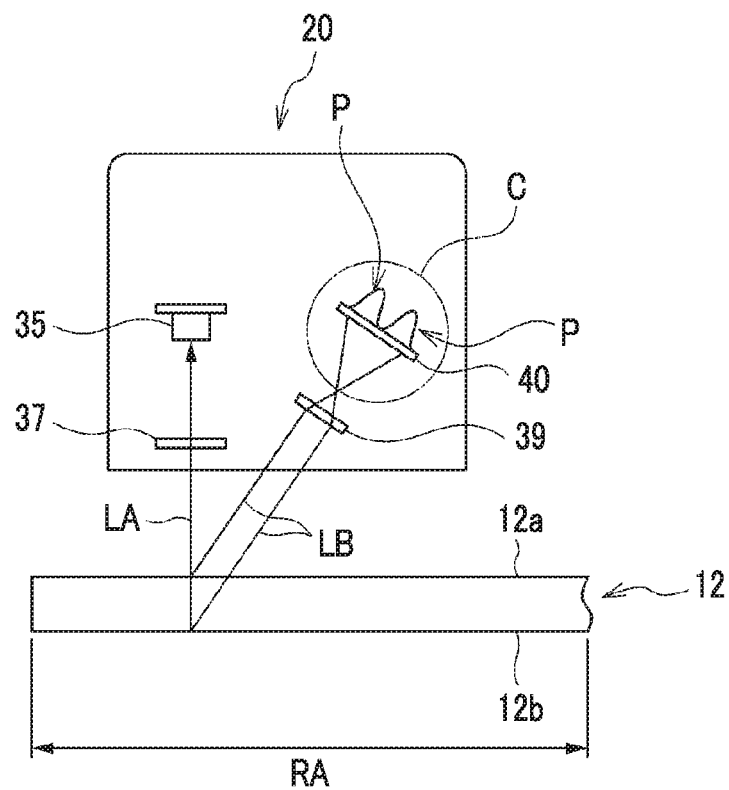
FIG. 5A is an illustrative diagram illustrating detection of a thickness of the mold in a laser displacement meter.
Figure 5B:
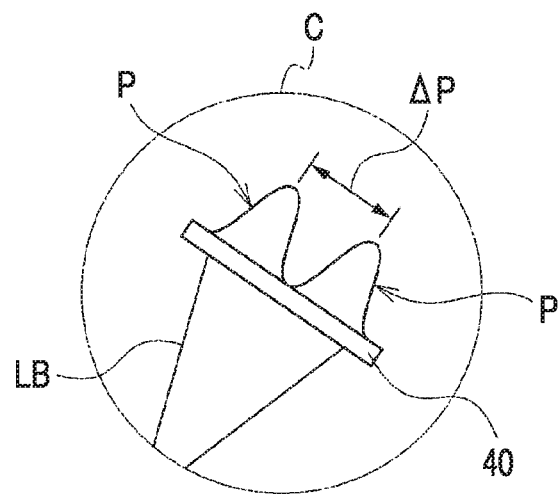
FIG. 5B is an enlarged view of the inside of a frame line C in FIG. 5A.

FIG. 5A is an illustrative diagram illustrating detection of the thickness W of the mold 12 in the laser displacement meter 20. FIG. 5B is an enlarged view of the inside of a frame line C in FIG. 5A. When the thickness W is detected, the incidence unit 30 of the laser displacement meter 20 functions as a second incidence unit of the present invention, and the detection unit 32 functions as a second detection unit of the present invention.

As illustrated in FIGS. 4 and 5A, when the thickness W of the mold 12 is detected, the laser light LA is vertically incident on the non-formation region RA that is a region in which the needle-shaped recess 14 is not formed in the mold 12 by the incidence unit 30 of the laser displacement meter 20. The laser light LA is diffused and reflected by the first surface 12a of the non-formation region RA, and is incident on the mold 12 (non-formation region RA) from the first surface 12a and diffused and reflected by the second surface 12b. Thus, the reflection light LB diffused and reflected by the first surface 12a and the reflection light LB diffused and reflected by the second surface 12b are incident respectively as spotlights on the imaging surface of the imaging element 40 of the detection unit 32. The reflection light LB diffused and reflected by the first surface 12a is laser light LA emitted from the first surface 12a by the laser light LA being reflected by the first surface 12a, and corresponds to the measurement wave emitted from the first surface of the present invention. Further, the reflection light LB diffused and reflected by the second surface 12b is laser light LA emitted from the second surface 12b by the laser light LA being reflected by the second surface 12b, and corresponds to the measured wave emitted from the second surface of the present invention.

As illustrated in FIG. 5B, in the imaging element 40, the light reception signals (corresponds to a second detection result of the present invention) corresponding to the reflection light LB at the first surface 12a and the reflection light LB at the second surface 12b are detected. An interval ΔP of the peaks P of the light reception signals respectively corresponding to both of beams of the reflection light LB is information indicating the thickness W of the mold 12. Therefore, it is possible to detect the thickness W of the mold 12 by measuring the interval ΔP of the peaks P of the light reception signals respectively corresponding to both of beams of the reflection light LB on the basis of the light reception signal output from the imaging element 40.

The laser light LA is incident on the plurality of points of the non-formation region RA of the mold 12, the thicknesses W of the mold 12 at the plurality of points are detected, and an average value of the thicknesses W of the plurality of points may be used as the thickness W of the mold 12.

Further, a method of detecting the thickness W of the mold 12 using a laser displacement meter 20 is not limited to the method of measuring the interval ΔP of the peak P and, for example, a known method of analyzing an interference fringe between reflection light LB at the first surface 12a and reflection light LB at the second surface 12b may be used.

[Detection of Height Hb]

Figure 6:
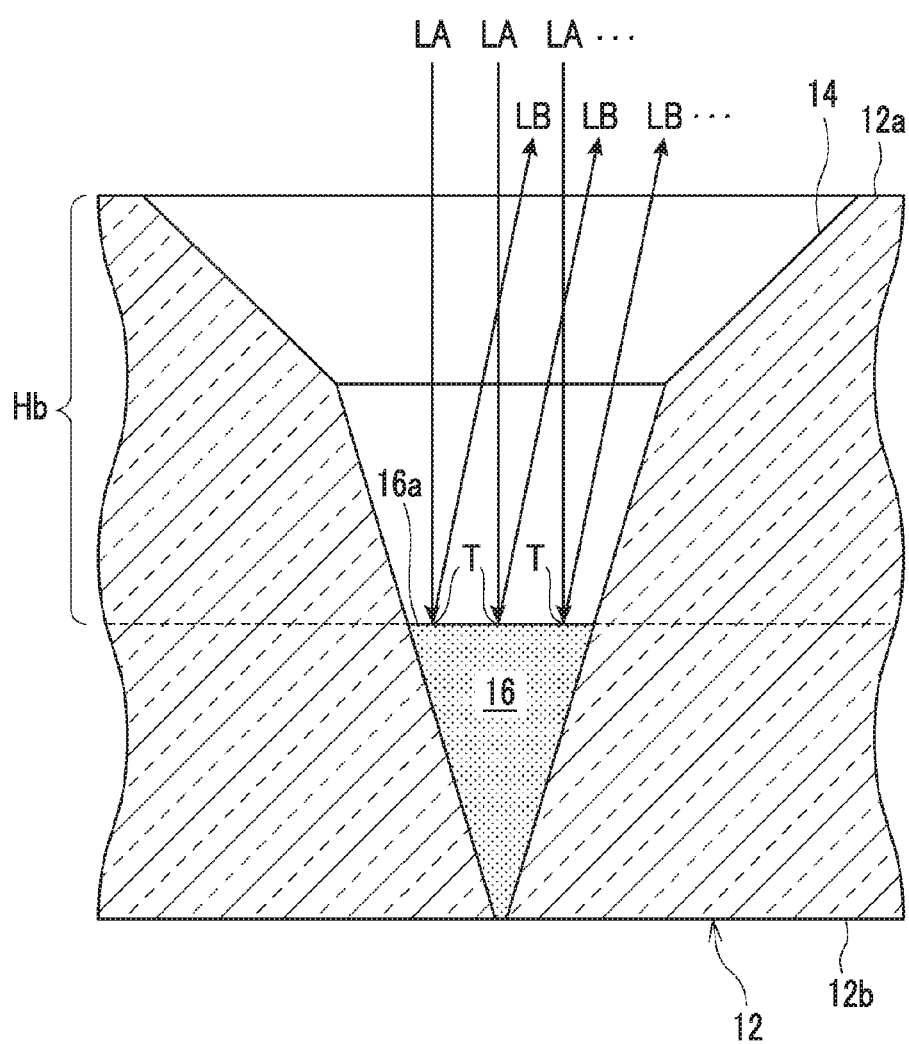
FIG. 6 is an illustrative diagram illustrating detection of a height Hb in FIG. 4 using a laser displacement meter.

FIG. 6 is an illustrative diagram illustrating detection of the height Hb in the laser displacement meter 20. When the height Hb is detected, the incidence unit 30 of the laser displacement meter 20 functions as a first incidence unit of the present invention, and the detection unit 32 functions as a first detection unit of the present invention.

As illustrated in FIG. 6, in a case where the height Hb is detected, laser light LA is sequentially vertically (including substantially vertically as described above) incident on a plurality of positions (a plurality of points) T of the drug surface 16a in each needle-shaped recess 14 by the incidence unit 30 of the laser displacement meter 20. Positions and the number of the plurality of positions T are not particularly limited, and it is preferable for the plurality of positions T to be evenly distributed on the drug surface 16a. The laser light LA is diffused and reflected at the plurality of positions T.

Here, in this embodiment, when the thickness W of the above-described mold 12 is detected, the light reception signal corresponding to the reflection light LB at the first surface 12a is detected, and therefore, incidence of the laser light LA on the first surface 12a of the mold 12 (non-formation region RA) is omitted. When the height Hb is detected, incidence of the laser light LA on the first surface 12a of the mold 12 and detection of the light reception signal corresponding to reflection light LB thereof may be performed.

The reflected beam LB of the laser light LA diffused and reflected respectively at a plurality of positions T is sequentially incident as spot light on the imaging surface of the imaging element 40 of the detection unit 32. Thus, the imaging element 40 sequentially detects the light reception signal (corresponding to a first detection result of the present invention) corresponding to the reflection light LB diffused and reflected respectively at the plurality of positions T. This reflection light LB corresponds to a measurement wave emitted from the drug surface of the present invention.

On the basis of an interval between a peak (not illustrated) of the light reception signal corresponding to the reflection light LB at the plurality of positions T and a peak (not illustrated) of the light reception signal corresponding to the reflection light LB of the first surface 12a obtained previously, a height from each of the plurality of positions T to the first surface 12a can be detected. In this embodiment, an average value of the height from each of the plurality of positions T to the first surface 12a is detected as the height Hb from the drug surface 16a of the needle-shaped recess 14 to the first surface 12a. The height Hb is detected for each needle-shaped recess 14. The height Hb from each of a plurality of positions T to the first surface 12a may be detected for each needle-shaped recess 14 instead of detecting the average value of the height Hb from each of a plurality of positions T to the first surface 12a for each needle-shaped recess 14. Accordingly, the surface shape of the drug surface 16a can be detected for each needle-shaped recess 14.

A method of detecting the height Hb of each needle-shaped recess 14 using the laser displacement meter 20 is not limited to the above-described method, and a known method may be used.

[Detection of Height Ht]

Referring back to FIG. 4, the height Ht from the second surface 12b to the drug surface 16a in the needle-shaped recess 14 can be detected by subtracting the height Hb of each needle-shaped recess 14 from the thickness W of the mold 12. The detection of the height Ht of each needle-shaped recess 14 is performed by the device body 21 that will be described below. In a case where the height Hb from each of the plurality of positions T to the first surface 12a is detected for each needle-shaped recess 14 as described above, the height Ht from the second surface 12b to each of the plurality of positions T is detected for each needle-like recess 14. The device body 21 obtains the volume of the drug 16 filled in each needle-shaped recess 14 on the basis of the detection result of the height Ht of each needle-shaped recess 14.

[Configuration of Device Body]

Figure 7:
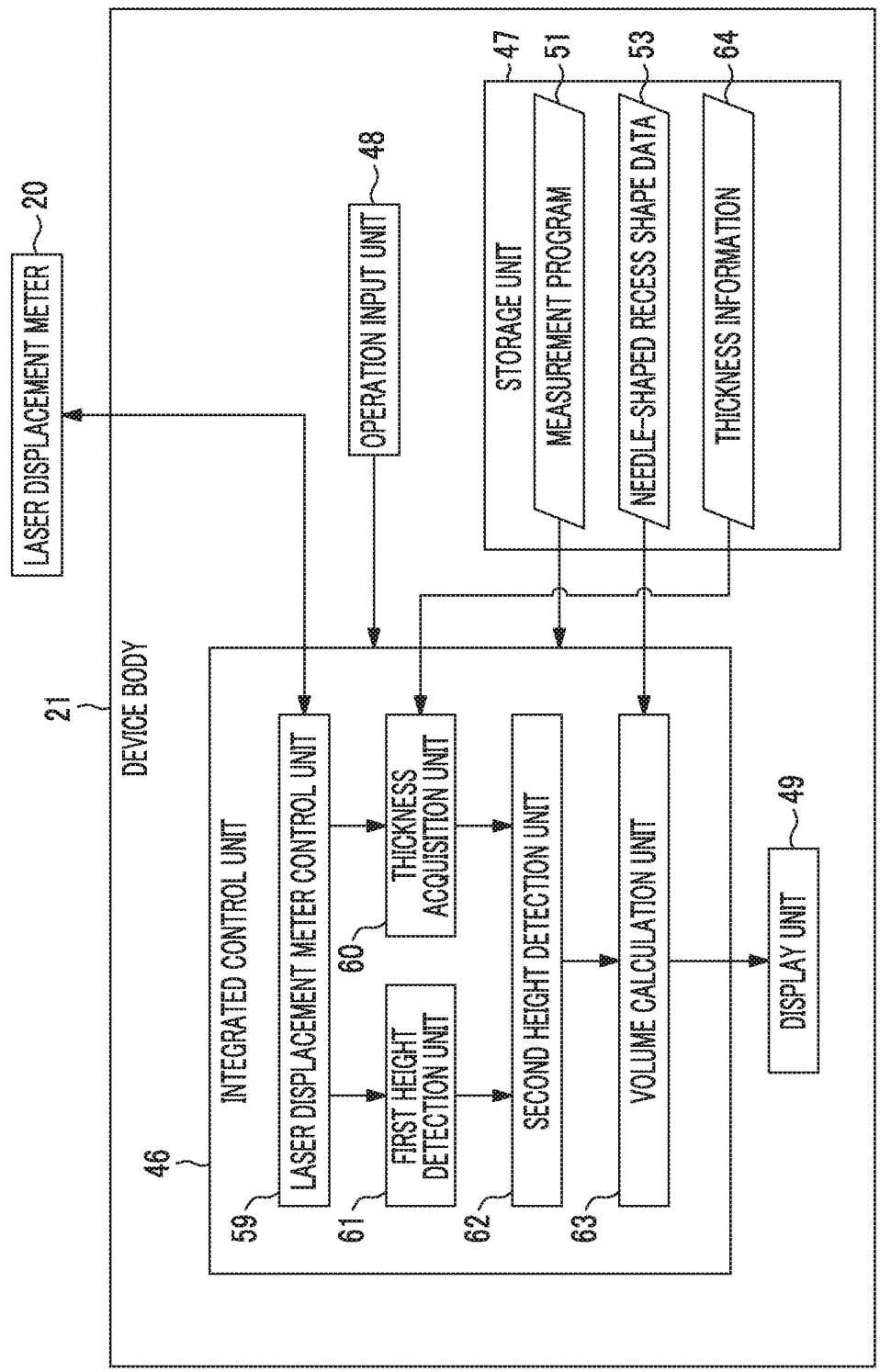
FIG. 7 is a block diagram illustrating an electrical configuration of a device body.

FIG. 7 is a block diagram illustrating an electrical configuration of the device body 21. This device body 21 analyzes the light reception signal input from the laser displacement meter 20, detects the height Hb of each needle-shaped recess 14, and obtains the volume of the drug 16 of each needle-shaped recess 14 on the basis of the detection result. As such a device body 21, for example, a personal computer (including a monitor), a dedicated calculation device, or the like can be used.

As illustrated in FIG. 7, the device body 21 mainly includes an integrated control unit 46, a storage unit 47, an operation input unit 48, and a display unit 49.

The integrated control unit 46 includes, for example, various calculation units or processing units including a central processing unit (CPU), and executes various programs or information read from the storage unit 47 on the basis of the control signal from the operation input unit 48 to control the entire measurement device 10 including the device body 21 in an integrated manner. Further, the integrated control unit 46 will be described below in detail, and calculates the volume of the drug 16 of each needle-shaped recess 14.

Various types of information including a measurement program 51 and needle-shaped recess data 53 are stored in the storage unit 47. The measurement program 51 corresponds to the program of the present invention, and causes the integrated control unit 46 (a computer of the measurement device 10) to function as means for measuring the volume of the drug 16 in each needle-shaped recess 14.

The needle-shaped recess shape data 53 is obtained by measuring the shape (including a size) of the needle-shaped recess 14 formed in the mold 12 in advance. As the needle-shaped recess shape data 53, data obtained by actually measuring the shape of the needle-shaped recesses 14 using a known scheme may be used or data measured by a manufacturer of the mold 12 in advance may be used.

The operation input unit 48 is used, for example, for an operation of starting the measurement in the measurement device 10. Further, the display unit 49 is, for example, a liquid crystal display, and displays a result of calculating the volume of the drug 16 in the integrated control unit 46, or the like.

[Configuration of Integrated Control Unit]

The integrated control unit 46 executes the measurement program 51 read from the storage unit 47 to function as a laser displacement meter control unit 59, a thickness acquisition unit 60, a first height detection unit 61, a second height detection unit 62, and a volume calculation unit 63.

The laser displacement meter control unit 59 performs wired or wireless connection (including a connection over a communication network such as the Internet) to the laser displacement meter 20. This laser displacement meter control unit 59 controls each unit (such as the driving circuit 36 or the imaging element 40) of the laser displacement meter 20 on the basis of a control signal from the operation input unit 48, to cause the laser displacement meter 20 to execute incidence of the laser light LA on the mold 12 and detection of the reflection light LB. Further, the laser displacement meter control unit 59 acquires the light reception signal of the reflection light LB detected by the laser displacement meter 20 from the laser displacement meter 20.

More specifically, the laser displacement meter control unit 59 functions as a reference surface height acquisition unit of the present invention together with the laser displacement meter 20 and the thickness acquisition unit 60 to be described below at the time of detection of the thickness W of the mold 12 described above, and acquires the light reception signal (a second detection result of the present invention) corresponding to the reflection light LB at the first surface 12a and the reflection light LB at the second surface 12b from the laser displacement meter 20. The laser displacement meter control unit 59 outputs the light reception signal acquired from the laser displacement meter 20 to the thickness acquisition unit 60. The laser displacement meter control unit 59 outputs the light reception signal corresponding to the reflection light LB at the first surface 12a to the first height detection unit 61.

On the other hand, the laser displacement meter control unit 59 functions as a detection result acquisition unit of the present invention together with the laser displacement meter 20 at the time of detection of the height Hb described above, and acquires a light reception signal (a first detection result of the present invention) corresponding to the reflection light LB at the plurality of positions T of each needle-shaped recess 14 from the laser displacement meter 20. The laser displacement meter control unit 59 outputs the light reception signal acquired from the laser displacement meter 20 to the first height detection unit 61.

The thickness acquisition unit 60 detects (acquires) the thickness W of the mold 12 that is a height between the first surface 12a and the second surface 12b (that is, the reference surface height of the present invention) on the basis of the light reception signal input from the laser displacement meter control unit 59, that is, the light reception signal corresponding to the reflection light LB at the first surface 12a and the light reception signal corresponding to the reflection light LB at the second surface 12b. For example, the thickness acquisition unit 60 detects the thickness W of the mold 12 on the basis of the result of measuring the interval ΔP between the peaks P of the light reception signals respectively corresponding to both of beams of the reflection light LB as described above (see FIG. 5B). The thickness acquisition unit 60 outputs a result of the detection of the thickness W of the mold 12 to the second height detection unit 62.

In this case, in a case where the thickness W of the mold 12 is measured in advance and known, the thickness information 64 indicating the thickness W may be stored in the storage unit 47 in advance. Thus, the thickness acquisition unit 60 can acquire the thickness W of the mold 12 from the thickness information 64 stored in the storage unit 47. The thickness information 64 may be stored in a storage unit in a device (for example, a server or a database on the Internet, or various devices that can be connected with the device body 21) separate from the device body 21, instead of being stored in the storage unit 47. By acquiring the thickness information 64 in this way, the measurement in the laser displacement meter 20 can be omitted and the thickness W of the mold 12 can be simply acquired.

The first height detection unit 61 detects the height Hb of each needle-shaped recess 14 on the basis of the light reception signal input from the laser displacement meter control unit 59, that is, the light reception signal corresponding to the reflection light LB at the first surface 12a and the light reception signal corresponding to the reflection light LB at the plurality of positions T of each needle-shaped recess 14. For example, the first height detection unit 61 detects the height from each of the plurality of positions T in each needle-shaped recess 14 to the first surface 12a on the basis of the interval between the peak of the light reception signal corresponding to the reflection light LB at the first surface 12a and the peak of the light reception signal corresponding to the reflection light LB at the plurality of positions T in each needle-shaped recess 14, as described above (see FIG. 6). Then, the first height detection unit 61 detects the average value of the height from the plurality of positions T of each needle-shaped recess 14 to the first surface 12a, as the height Hb of each needle-shaped recess 14. The first height detection unit 61 outputs the detection result of the height Hb of each needle-shaped recess 14 to the second height detection unit 62.

The second height detection unit 62 subtracts the detection result of the height Hb of each needle-shaped recess 14 which is input from the first height detection unit 61 from the detection result of the thickness W of the mold 12 which is input from the thickness acquisition unit 60 to detect the height Ht of each needle-shaped recess 14. The second height detection unit 62 outputs the detection result of the height Ht of each needle-shaped recess 14 to the volume calculation unit 63.

As described above, the height Hb from each of the plurality of positions T to the first surface 12a may be detected for each needle-shaped recess 14 by the first height detection unit 61, the height Ht from the second surface 12b to each of the plurality of positions T may be detected for each needle-shaped recess 14 by the second height detection unit 62, and a result of the detection of the height Ht may be output to the volume calculation unit 63.

Figure 8:
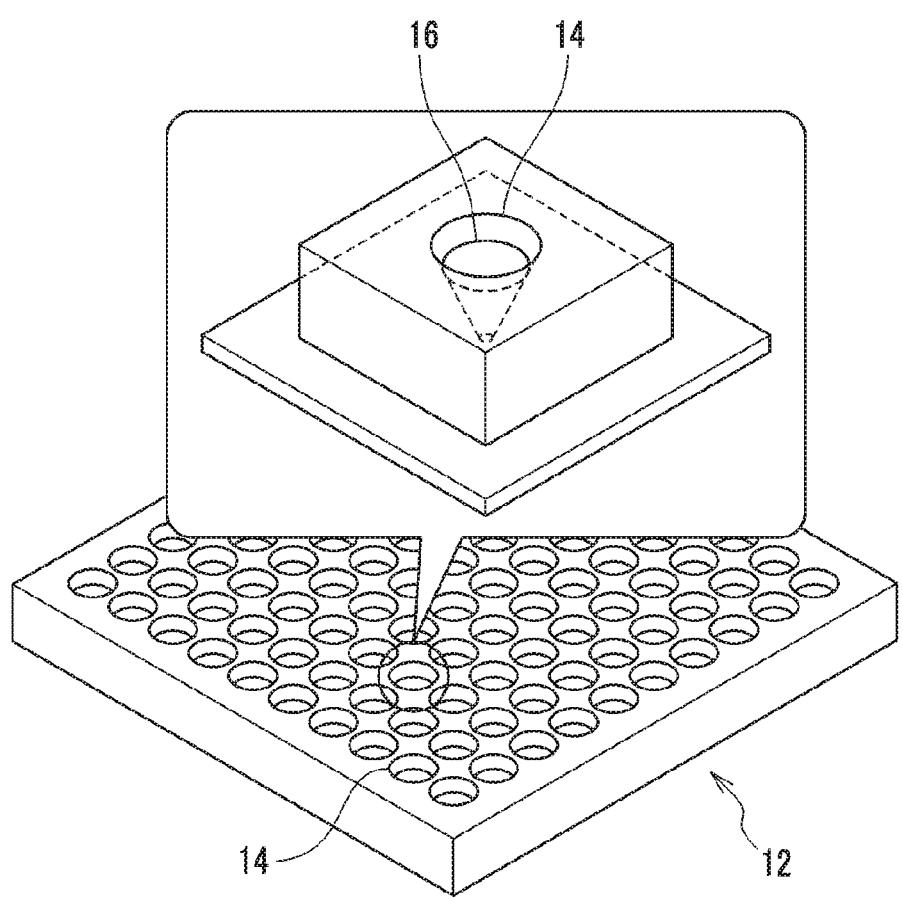
FIG. 8 is an illustrative diagram illustrating a process of calculating a volume of a drug in a needle-shaped recess in a volume calculation unit.

FIG. 8 is an illustrative diagram illustrating the process of calculating the volume of the drug 16 in the needle-shaped recess 14 in the volume calculation unit 63. As illustrated in FIG. 8, the height Ht of the drug surface 16a in each needle-shaped recess 14 is known on the basis of the detection result of the height Ht of each needle-shaped recess 14 which is input from the second height detection unit 62. Further, the shape of the individual needle-shaped recesses 14 is also known on the basis of the needle-shaped recess shape data 53 stored in the storage unit 47. Therefore, the volume calculation unit 63 calculates the capacity (volume) of the drug 16 of each needle-shaped recess 14 from the detection result of the height Ht of the drug surface 16a of each needle-shaped recess 14 and the shape of the individual needle-shaped recess 14 based on the needle-shaped recess shape data 53 read from the storage unit 47. Here, "to calculate the volume" is not limited to obtaining the volume of the drug 16 through calculation (computation) and, for example, may include obtaining a three-dimensional shape of the drug 16 in the needle-shaped recess 14 through simulation or the like or obtaining the volume using a data table (a relationship between a height Ht generated for every plurality of types of needle-shaped recess shape data 53 in advance and the volume).

Further, in a case where the height Ht from the second surface 12b to each of the plurality of positions T is detected for each needle-shaped recess 14 as described above, the height Ht of the plurality of positions of each needle-shaped recess 14 indicates the shape of the drug surface 16a of each needle-shaped recess 14. Therefore, the volume calculation unit 63 can calculate the volume of the drug 16 for each needle-shaped recess 14 more accurately from the height Ht of the plurality of positions of each needle-shaped recess 14 and the shape of the drug surface 16a, and the shape of the individual needle-shaped recess 14 based on the needle-shaped recess shape data 53.

The calculation result of the volume of the drug 16 for each needle-shaped recess 14 calculated by the volume calculation unit 63 is stored in the storage unit 47 as a measurement result of the volume of the drug 16 for each needle-shaped recess 14, and is displayed on the display unit 49.

Here, if a measurement time of the measurement device 10 is before solidification of the drug 16 (see FIGS. 3A and 3B), the volume of the drug 16 of each needle-shaped recess 14 which is calculated by the volume calculation unit 63 is the volume of the drug 16 in a solution state containing water or the like. In this case, the volume calculation unit 63 may calculate the volume of the drug component dissolved in the drug 16 in the needle-shaped recess 14. Here, the drug component refers to a drug itself (solute) which is dissolved in a solvent such as water. Further, the volume of the drug component is basically the same as that of the drug 16 after solidification of the needle-shaped recess 14.

Figure 9:
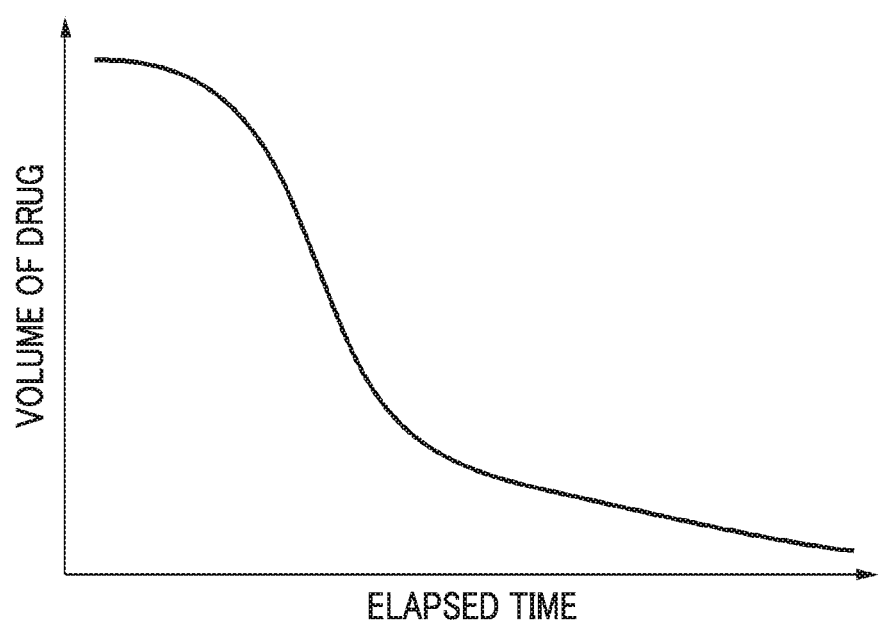
FIG. 9 is a graph illustrating a temporal change in a volume of a drug in a solution state filled in a needle-shaped recess.

FIG. 9 is a graph illustrating a temporal change in the volume of the drug 16 in a solution state filled in the needle-shaped recess 14. As illustrated in FIG. 9, the volume of the drug 16 in the needle-shaped recess 14 decreases over time due to evaporation of water, as illustrated in FIGS. 3A through 3C described above, but the volume of the drug component in the drug 16 does not change. Therefore, the concentration of the drug component in the drug 16 increases over time. Accordingly, the temporal change in the concentration of the drug component in the drug 16 in the needle-shaped recess 14 is obtained by obtaining the temporal change in the volume of the drug 16 in the needle-shaped recess 14 as illustrated in FIG. 9 in advance.

By measuring such a temporal change in concentration of the drug components in advance and storing the temporal change in the storage unit 47, the volume calculation unit 63 can obtain the concentration of the drug component at the time of measurement of the volume of the drug 16 described above. Thus, the volume calculation unit 63 may calculate the volume of the drug component of each needle-shaped recess 14 on the basis of the measurement result of the volume of the drug 16 in the solution state and the concentration of the drug component in the drug 16. The calculation result of the volume of the drug component is also stored in the storage unit 47 and displayed on the display unit 49.

Humidity around the mold 12 is adjusted to humidity of 100% (including substantially 100%) between the filling of the drug 16 in a solution state in the needle-shaped recess 14 and at least completion of the measurement in the measurement device 10 or an opening on the first surface 12a side of the needle-shaped recess 14 is covered with a transparent lid (such as a film), so that the evaporation of the water may be suppressed. Thus, a concentration of the drug component in the drug 16 in a solution state is substantially constant regardless of the elapse of time, and therefore, the volume of the drug component can be easily obtained from the measurement result of the volume of the drug 16.

Further, when the volume calculation unit 63 calculates the volume of the drug 16 for each needle-shaped recess 14 of the mold 12, a total volume of the drug 16 filled in the mold 12 may be calculated from the volume of the drug 16 of each needle-shaped recess 14. A result of the calculation of the total volume is also stored in the storage unit 47 as a measurement result of the total volume of the drug 16 in the entire mold 12 and displayed on the display unit 49.

The display unit 49 displays (for example, graphically displays) the volume of the drug 16 of each needle-shaped recess 14 calculated by the volume calculation unit 63, and the total volume of the drug 16 in the entire mold 12. Further, in a case where the display unit 49 displays the volume of the drug 16 of each needle-shaped recess 14 and the total volume of the drug 16 in the entire mold 12, the display unit 49 may perform a display of a predetermined allowable criterion of each of the volume and the total volume. Further, by providing, in the device body 21, a determination unit that determines whether or not each of the calculated volume and the calculated total volume of the drug 16 satisfies the allowable criterion, a determination result in the determination unit may also be displayed together by the display unit 49.

[Operation of Measurement Device]

Figure 10:
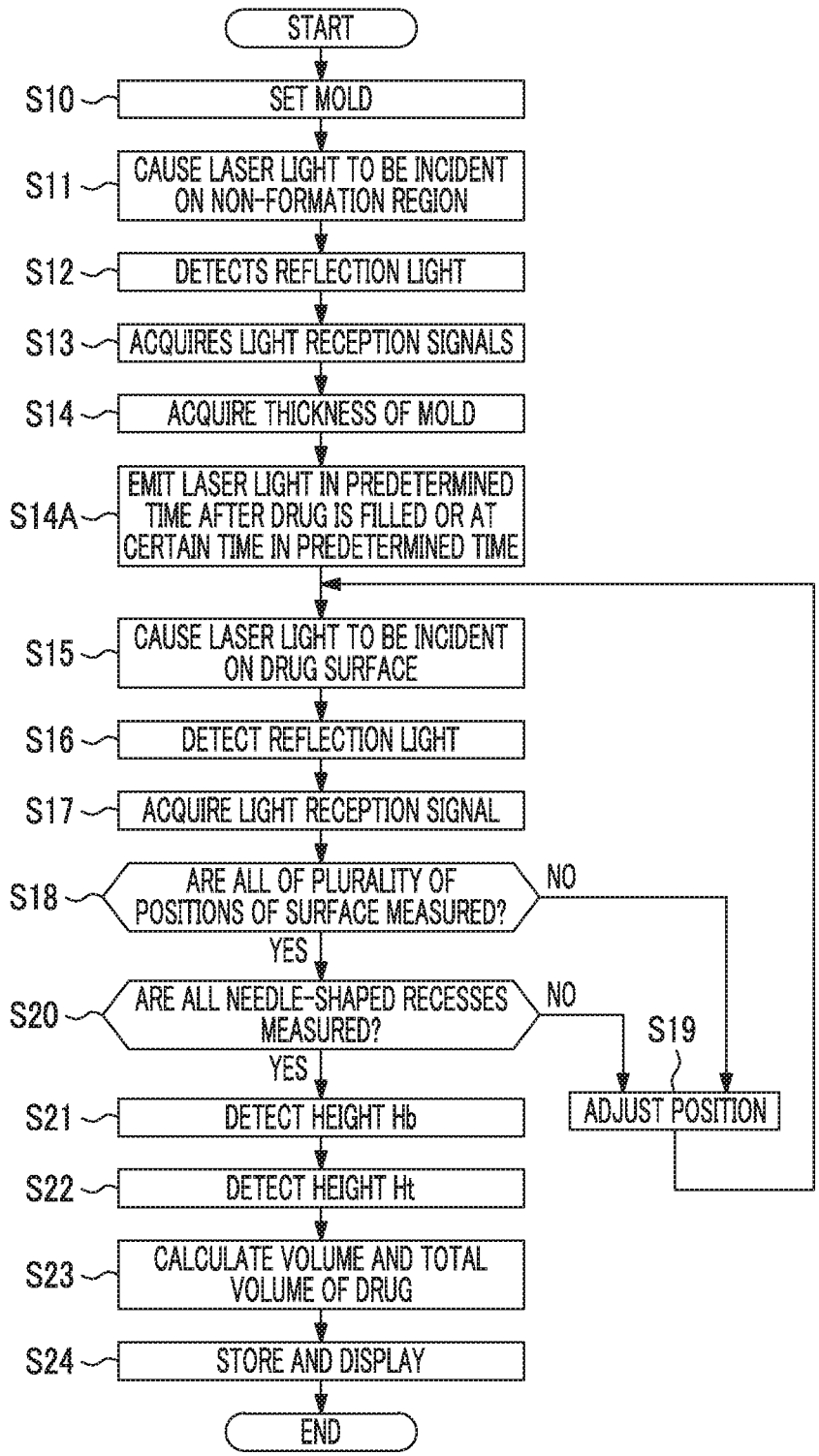
FIG. 10 is a flowchart illustrating a flow of a process of measuring a volume of a drug in each needle-shaped recess.

Next, an operation of the measurement device 10 having the above-described configuration, that is, a process of measuring the volume of the drug 16 of each needle-shaped recess 14 of the mold 12 (a measurement method of the present invention) will be described with reference to FIG. 10. FIG. 10 is a flowchart illustrating a flow of a process of measuring the volume of the drug 16 of each needle-shaped recess 14. The needle-shaped recess shape data 53 for the mold 12 that is a measurement target is stored in the storage unit 47 of the measurement device 10 in advance.

As illustrated in FIG. 10, the operator sets the mold 12 on the stage 19 of the measurement device 10 after filling the drug 16 in the solution state in the needle-shaped recess 14 of the mold 12 (step S10). Then, the operator performs adjustment of the position of the stage 19 using the above-described camera or the like and a position adjustment mechanism to align the incidence position of the laser light LA by the laser displacement meter 20 with the non-formation region RA of the mold 12.

If the operator performs a measurement start operation in the operation input unit 48 after adjusting the position of the stage 19, the laser displacement meter control unit 59 of the integrated control unit 46 performs a measurement start command with respect to the laser displacement meter 20. The driving circuit 36 of the laser displacement meter 20 receives this measurement start command and emits the laser light LA from the semiconductor laser light source 35. Thus, the incidence unit 30 of the laser displacement meter 20 causes the laser light LA to be incident on the non-formation region RA of the mold 12 from the first surface 12a of the mold 12 (step S11, which corresponds to a second incidence step of the present invention).

The laser light LA incident on the non-formation region RA of the mold 12 is diffused and reflected by the first surface 12a in the non-formation region RA, is incident on the inside of the mold 12 from the first surface 12a, and is diffused and reflected by the second surface 12b. The reflection light LB diffused and reflected by the first surface 12a and the reflection light LB diffused and reflected by the second surface 12b are incident as spot light on the imaging surface of the imaging element 40 of the detection unit 32. Thus, the imaging element 40 detects the reflection light LB on the first surface 12a and the reflection light LB on the second surface 12b (step S12, which corresponds to a second detection step of the present invention).

The light reception signals corresponding to both the reflection light LB detected by the imaging element 40 are amplified by the signal amplification circuit 41, and then, are output to the laser displacement meter control unit 59 of the device body 21. Thus, the laser displacement meter control unit 59 acquires the light reception signals corresponding to both the reflection light LB (step S13). The laser displacement meter control unit 59 outputs the light reception signals corresponding to both the reflection light LB to the thickness acquisition unit 60. The laser displacement meter control unit 59 outputs the light reception signals corresponding to the reflection light LB at the first surface 12a to the first height detection unit 61.

The thickness acquisition unit 60 measures an interval ΔP between peaks P of the light reception signals corresponding to both the reflection light LB as illustrated in FIG. 5B described above on the basis of the light reception signal acquired from the laser displacement meter control unit 59, and detects (acquires) the thickness W of the mold 12 corresponding to a reference surface height of the present invention (step S14, which corresponds to a reference surface height acquisition step of the present invention). As described above, in a case where the thickness W of the mold 12 that has been measured in advance is stored as the thickness information 64 in the storage unit 47, the thickness acquisition unit 60 may acquire the thickness W of the mold 12 from the thickness information 64 stored in the storage unit 47 (see FIG. 7). In this case, the process from step S11 to step S13 can be omitted. The thickness acquisition unit 60 outputs a detection result (acquisition result) of the thickness W of the mold 12 to the second height detection unit 62.

In a case where the thickness W of the mold 12 is detected using the laser displacement meter 20, a detection result of this thickness W is stored as the thickness information 64 in the storage unit 47 or the like. Therefore, in next measurements using the same mold 12, the process from step S11 to step S13 can be omitted.

Then, the operator causes emission of the laser light LA from the laser displacement meter 20 to the drug surface 16a in each needle-shaped recess 14 to be started. The emission of the laser light LA is started within a predetermined time (for example, within 5 minutes) after the drug 16 is filled in each needle-shaped recess 14 or at a certain time within a predetermined time when measurement of the volume of the drug 16 in a solution state is performed (step S14A). Accordingly, the measurement can be started while there is no significant change in a state of the drug 16 filled in each needle-shaped recess 14. Further, by starting the measurement at a constant time within a predetermined time, measurement of the volume of the drug 16 in the needle-shaped recesses 14 can always be performed under the same conditions even in a case where the water evaporates from the drug 16. The operator performs the position adjustment of the stage 19 using the above-described camera or the like and the position adjustment mechanism to align the incidence position of the laser light LA by the laser displacement meter 20 with a first point among the plurality of positions T on the drug surface 16a (illustrated as an appropriate "surface" in the drawing) in one needle-shaped recess 14.

If the operator performs a measurement start operation in the operation input unit 48 after adjusting the position of the stage 19, the laser displacement meter control unit 59 performs a measurement start command with respect to the laser displacement meter 20. The incidence unit 30 of the laser displacement meter 20 receives the measurement start command and causes the laser light LA to be incident on a first point on the drug surface 16*a* in the needle-shaped recess 14 from the first surface 12*a* of the mold 12 (step S15, which corresponds to a first incidence step of the present invention).

The laser light LA incident on the first point of the drug surface 16*a* is diffused and reflected at the first point. The reflection light LB diffused and reflected at the first point of the drug surface 16*a* is incident as spot light on the imaging surface of the imaging element 40 of the detection unit 32. Thus, the imaging element 40 detects the reflection light LB at the first point of the drug surface 16*a* (step S16, which corresponds to a first detection step of the present invention).

The light reception signal corresponding to the reflection light LB at the first point of the detected drug surface 16*a* by the imaging element 40 is amplified by the signal amplification circuit 41 and output to the laser displacement meter control unit 59 of the device body 21. Thus, the laser displacement meter control unit 59 acquires the light reception signal corresponding to the reflection light LB at the first point of the drug surface 16*a* (step S17, which corresponds to a detection result acquisition step of the present invention). The laser displacement meter control unit 59 outputs the light reception signal corresponding to the reflection light LB at the first point of the drug surface 16*a* to the first height detection unit 61.

The operator performs adjustment of the position of the stage 19 using the above-described camera or the like and the position adjustment mechanism to align the incidence position of the laser light LA by the laser displacement meter 20 with a second point of the plurality of positions T of the drug surface 16*a* in the needle-shaped recesses 14 (NO in step S18, and step S19).

If an operator performs a measurement start operation in the operation input unit 48 after adjustment of the position of the stage 19, the incidence unit 30 of the laser displacement meter 20 causes the laser light LA to be incident on the second point of the drug surface 16*a* in the needle-shaped recess 14 under control of the laser displacement meter control unit 59 (step S15). The imaging element 40 of the detection unit 32 detects the reflection light LB diffused and reflected at the second point of the drug surface 16*a* (step S16), the signal amplification circuit 41 amplifies the light reception signal and outputs the light reception signal to the device body 21, and the laser displacement meter control unit 59 acquires the light reception signal and outputs the light reception signal to the first height detection unit 61 (step S17).

Hereinafter, similarly, the process from step S15 to the step S17 described above is repeatedly executed at all of the plurality of positions T of the drug surface 16*a* in the needle-shaped recess 14 (YES in step S18). Thus, the light reception signal corresponding to the reflection light LB diffused and reflected respectively at the plurality of positions T of the drug surface 16*a* in one needle-shaped recess 14 is input to the first height detection unit 61.

Then, a process from step S15 to step S19 described above is similarly repeatedly executed for the drug surface 16*a* in the other needle-shaped recess 14 of the mold 12 (NO in step S20). Thus, the light reception signal corresponding to the reflection light LB that is diffused and reflected respectively at the plurality of positions T of the drug surface 16*a* of each needle-shaped recess 14 is input to the first height detection unit 61 (YES in step S20).

The first height detection unit 61 measures an interval between a peak of the light reception signal corresponding to the reflection light LB at the first surface 12*a* and a peak of the light reception signal corresponding to the reflection light LB at the plurality of positions T of each needle-shaped recess 14 on the basis of the light reception signal acquired from the laser displacement meter control unit 59, and detects the height from each of the plurality of positions T of each needle-shaped recess 14 to the first surface 12*a* (see FIG. 6). Then, the first height detection unit 61 detects the average value of the height from the plurality of positions T of each needle-shaped recess 14 to the first surface 12*a*, as the height Hb of each needle-shaped recess 14 (step S21, which corresponds to a first height detection step of the present invention). The first height detection unit 61 outputs a result of detection of the height Hb of each needle-shaped recess 14 to the second height detection unit 62.

In step S21, the height Hb from each of the plurality of positions T to the first surface 12*a* may be detected for each needle-shaped recess 14 instead of detecting the average value of the height Hb from each of the plurality of positions T to the first surface 12*a* for each needle-shaped recess 14.

The second height detection unit 62 subtracts the detection result of the height Hb of each needle-shaped recess 14 which is input from the first height detection unit 61 from the detection result of the thickness W of the mold 12 which is input from the thickness acquisition unit 60. Thus, the second height detection unit 62 detects the height Ht of each needle-shaped recess 14 (step S22, which corresponds to a second height detection step of the present invention). The second height detection unit 62 outputs a result of the detection of the height Ht of each needle-shaped recess 14 to the volume calculation unit 63. In a case where the height Hb from each of the plurality of positions T to the first surface 12*a* is detected for each needle-shaped recess 14 in step S21, the height Ht from the second surface 12*b* to each of a plurality of positions T is detected for each needle-shaped recess 14 in step S22.

The volume calculation unit 63 calculates the capacity (volume) of the drug 16 filled in each needle-shaped recess 14 on the basis of the detection result of the height Ht of each needle-shaped recess 14 which is input from the second height detection unit 62, and the needle-shaped recess shape data 53 read from the storage unit 47 (step S23, which corresponds to a volume calculation step of the present invention). In a case where the height Ht from the second surface 12*b* to each of the plurality of positions T is detected for each needle-shaped recess 14 in step S22, the volume of the drug 16 of each needle-shaped recess 14 is calculated from the height Ht at a plurality of positions of each needle-shaped recess 14 and a shape of the drug surface 16*a*, and the shape of the individual needle-shaped recess 14 based on the needle-shaped recess shape data 53 in step S23. Accordingly, since the surface shape of the drug surface 16*a* in the needle-shaped recess 14 is reflected in the calculation of the volume of the drug 16, the volume of the drug 16 of each needle-shaped recess 14 can be calculated more accurately.

Further, the volume calculation unit 63 sums the volumes of the drug 16 of the respective needle-shaped recesses 14 of the mold 12, and calculates a total volume of the drug 16 filled in the mold 12.

The volume calculation unit 63 outputs the calculation result of the volume of the drug 16 of each needle-shaped recess 14 and the calculation result of the total volume of the drug 16 in the entire mold 12 to the storage unit 47 and the display unit 49. Thus, the calculation result of the volume of the drug 16 of each needle-shaped recess 14 and the calculation result of the total volume of the drug 16 in the entire mold 12 are stored in the storage unit 47 and displayed on the display unit 49 as the measurement result of the volume of the drug 16 of each needle-shaped recess 14 and the measurement result of the total volume of the drug 16 (step S24). Further, an allowable criterion of each of the volume and the total volume of the drug 16 is displayed, and a determination result of determining whether each of the volume and the total volume of the drug 16 satisfies the allowable criterion is displayed on the display unit 49.

Here, if a measurement time in the measurement device 10 is before solidification of the drug 16, the measurement device 10 measures the volume of the drug 16 (including water) in a solution state in each needle-shaped recess 14 (see FIGS. 3A and 3B). On the other hand, if the measurement time in the measurement device 10 is after the solidification of the drug 16, the measurement device 10 measures the volume of the drug 16 in a solid form in each needle-shaped recess 14 (see FIG. 3C). Thus, the measurement device 10 can measure the volume of the drug 16 filled in the needle-shaped recess 14 using the same measurement method regardless of a state of the drug 16 in the needle-shaped recesses 14.

In a case where the measurement time in the measurement device 10 is before solidification of the drug 16, the volume calculation unit 63 acquires a concentration of the drug component in the measurement of the volume of the drug 16 in a solution state, as described above. The volume calculation unit 63 calculates the volume of the drug component of each needle-shaped recess 14 on the basis of a result of the measurement of the volume of the drug 16 in the solution state and the concentration of the drug component in the drug 16. A result of this calculation is also stored in the storage unit 47 and displayed on the display unit 49.

A process of measuring the volume of the drug 16 in the measurement device 10 is all completed.

The measurement result of the volume of the drug 16 of each needle-shaped recess 14 obtained by the measurement device 10 is fed back to the filling device that fills the drug 16 in a solution state in each needle-shaped recess 14 of the mold 12. For example, the step of filling the drug 16 in the filling device includes a coating step of coating the first surface 12a of the mold 12 with the drug 16, and a step of removing an extra drug 16 on the first surface 12a using a brush, a scraper, or the like to form a thin film of the drug 16 on the first surface 12a. The coating step or the removing step is a step that affects the volume of the drug 16 in each needle-shaped recess 14. Therefore, by controlling a coating speed of the coating step or a removal rate of the removing step according to the measurement result of the volume of the drug 16 (a magnitude or a variation in the volume) of each needle-shaped recess 14, the volume of the drug 16 in each needle-shaped recess 14 can be appropriately adjusted.

Effects of First Embodiment

Thus, in the measurement device 10 of the first embodiment, since the volume of the drug 16 in each needle-shaped recess 14 is measured on the basis of the detection result of the reflection light LB reflected by the mold 12 according to the incidence of the laser light LA, it is possible to nondestructively measure the volume of the drug 16 for each needle-shaped recess 14 of the mold 12 with high precision. There is a merit that the measurement device 10 can perform the measurement without changing a measurement method even when a type of the drug 16 is changed.

Modification Example of First Embodiment

Figure 11:
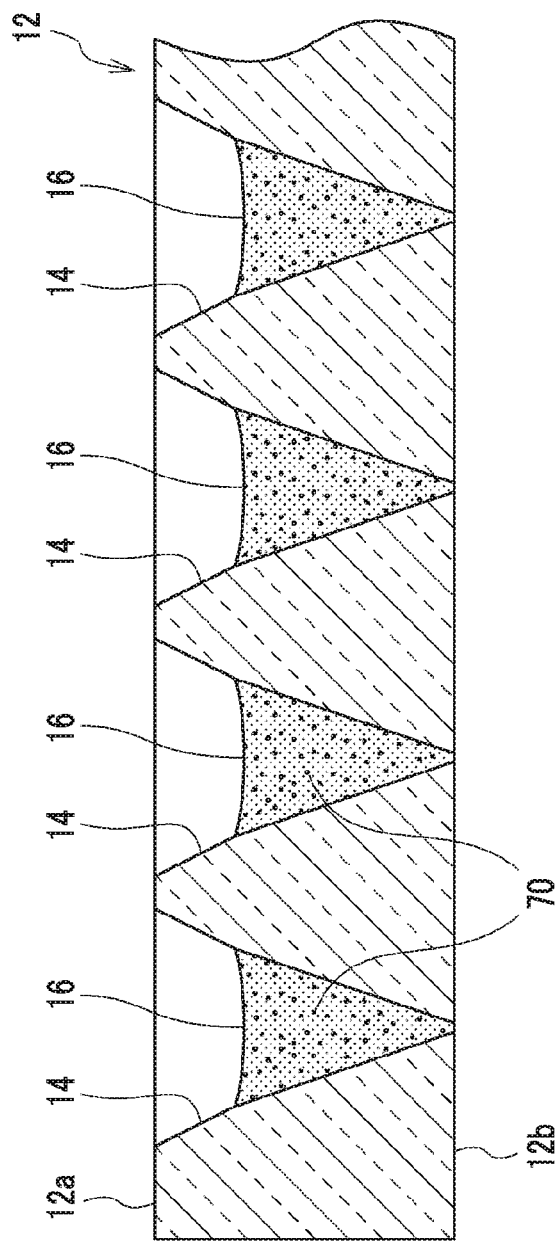
FIG. 11 is a cross-sectional view of a mold of a modification example of the first embodiment in which a drug to which a dye has been added is filled in a needle-shaped recess.

In the first embodiment, when the drug 16 filled in the needle-shaped recess 14 is transparent, it may be difficult to align the incidence position of the laser light LA by the laser displacement meter 20 with the drug surface 16a of the needle-shaped recess 14. Therefore, as illustrated in FIG. 11, a dye 70 may be added to the drug 16 filled in the needle-shaped recess 14. FIG. 11 is a cross-sectional view of a mold 12 of a modification example of the first embodiment in which the drug 16 to which the dye 70 has been added is filled in the needle-shaped recess 14.

The dye 70 is not particularly limited as long as the dye is harmless to the human body and, for example, Evans Blue can be used. Since the Evans blue remains in the drug 16 even when the water contained in the drug 16 in a solution state evaporates, the drug 16 in the needle-shaped recess 14 becomes identifiable even after the drug 16 is solidified. Thus, by adding the dye 70 to the drug 16 filled in the needle-shaped recess 14, it is possible to easily align the incidence position of the laser light LA by the laser displacement meter 20 with the drug surface 16a of the needle-shaped recess 14.

Although surface treatment is not performed on the first surface 12a of the mold 12 in the first embodiment, for example, hydrophilic treatment such as Teflon (registered trademark) treatment may be performed on the first surface 12a in advance prior to filling of the drug 16 into the needle-shaped recess 14. FIG. 12A is a cross-sectional view of the mold 12 in which hydrophilic treatment is not performed on the first surface 12a, and FIG. 12B is a cross-sectional view of the mold 12 in which the hydrophilic treatment is performed on the first surface 12a.

As illustrated in FIG. 12A, in the mold 12 in which the hydrophilic treatment is not performed on the first surface 12a, meniscus is generated on the drug surface 16a in the needle-shaped recess 14. On the other hand, as illustrated in FIG. 12B, in the mold 12 in which the hydrophilic treatment is performed on the first surface 12a in advance before the drug 16 is filled in the needle-shaped recess 14, the meniscus is prevented from being generated on the drug surface 16a in the needle-shaped recess 14, and the drug surface 16a may be a plane. Thus, an error between the height Ht detected by the second height detection unit 62 described above and an actual height of the entire drug surface 16a of the needle-shaped recess 14 is reduced. As a result, it is possible to measure the volume of the drug 16 of each needle-shaped recess 14 with higher accuracy.

In the first embodiment, a light diffusion, reflection, and reception type CCD (or CMOS) laser displacement meter using a triangular distance measurement scheme is used as the laser displacement meter 20, but a distance measurement scheme or type of the laser displacement meter is not particularly limited. For example, a specular reflection light reception type laser displacement meter may be used in place of the light diffusion, reflection, and reception type. Further, a laser displacement meter using a position sensing device (PSD) scheme may be used in place of the CCD (CMOS) laser displacement meter. Further, a laser displacement meter using a phase difference ranging scheme or a confocal scheme may be used in place of the triangular distance measurement scheme.

Although the laser light LA is incident on the non-formation region RA from the first surface 12a of the mold 12 by the laser displacement meter 20 when the thickness W of the mold 12 is detected in the first embodiment, the laser light LA may be incident on the non-formation region RA from the second surface 12b. Further, the thickness W of the mold 12 is detected using the laser displacement meter 20 arranged on the first surface 12a of the mold 12 in the first embodiment described above, the thickness W of the mold 12 may be detected using the laser displacement meter 20 arranged on both surfaces of the mold 12.

Although the thickness W of the mold 12 or the height Hb from the drug surface 16a of the drug 16 to the first surface 12a is detected using the laser displacement meter 20 in the first embodiment, various optical measurement devices capable of causing various types of measurement light (a measurement wave of the present invention) to be incident on the mold 12 and detecting reflection light thereof may be used in place of the laser displacement meter.

Although the operator manually performs the adjustment of the incidence position of the laser light LA from the laser displacement meter 20 when the thickness W of the mold 12 or the height Hb of each needle-shaped recess 14 is measured using a position adjustment mechanism in the first embodiment, the adjustment of the incidence position may be performed through the automatic control. In this case, it is possible to automatically perform the measurement in the measurement device 10. Thus, when the measurement device 10 is incorporated in an MNA manufacturing process, production of efficient MNA (for example, production using a Roll to Roll scheme) can be performed.

Although the measurement device 10 including the stage 19, the laser displacement meter 20, and the device body 21 has been described by way of example in the first embodiment, the measurement device of the present invention may include only the device body 21. That is, the present invention can also be applied to a measurement device that acquires a separately obtained detection result (light reception signal) of the laser displacement meter 20 via a recording medium such as a memory card, a communication network, or the like, and calculates the volume of the drug 16 on the basis of the acquired detection result.

Although one communicating hole 31 is formed in each needle-shaped recess 14 on the second surface 12b of the mold 12 in the first embodiment, a plurality of communication holes 31 may be formed in each needle-shaped recess 14. Further, a size of a diameter of the communication hole 31 may be appropriately changed.

Measurement Device of Second Embodiment

Although the measurement has been performed using the laser displacement meter 20 including one incidence unit 30 and one detection unit 32 (see FIG. 1) in the measurement device 10 of the first embodiment, the measurement may be performed using the laser displacement meter 20A in a line sensor form (see FIGS. 13A and 13B) including a plurality of incidence units 30 and a plurality of detection units 32.

FIG. 13A is a top view of the laser displacement meter 20A of the measurement device 10 of the second embodiment, and FIG. 13B is a side view of the laser displacement meter 20A. In FIG. 13A, illustration of the incidence unit 30 and the detection unit 32 is omitted in order to prevent complication of the drawings. Further, the measurement device 10 of the second embodiment has basically the same configuration as the measurement device 10 of the first embodiment except that the measurement device 10 of the second embodiment includes the laser displacement meter 20A in place of the laser displacement meter 20 (see FIG. 1), and components having the same function or configuration as in the first embodiment are denoted with the same reference signs and description thereof will be omitted.

As illustrated in FIGS. 13A and 13B, the laser displacement meter 20A has a shape extending in a direction (hereinafter referred to as a longitudinal direction) parallel to the first surface 12a and the second surface 12b of the mold 12. A plurality of sets of the incidence units 30 and the detection units 32 described with reference to FIG. 1 described above are provided in the longitudinal direction in the laser displacement meter 20A. Thus, the laser light LA can be caused to be incident on a plurality of positions (the first surface 12a, the drug surface 16a of the needle-shaped recess 14, and the like) of the mold 12 from a plurality of incidence units 30 at the same time in the longitudinal direction of the laser displacement meter 20A, and reflection light LB reflected at the plurality of positions can be simultaneously detected by a plurality of detection units 32.

In the second embodiment, incidence of the laser light LA by the plurality of incidence units 30 and detection of the reflection light LB by the plurality of detection units 32 are executed while relatively moving the laser displacement meter 20A with respect to the mold 12 in a lateral direction (a direction indicated by an arrow V in FIG. 13B) parallel to the first surface 12a and the second surface 12b of the mold 12 and vertical to a longitudinal direction using a relative movement unit (not illustrated). Thus, it is possible to scan the entire surface of the first surface 12a using the laser displacement meter 20A. Here, the "relative movement" is to move at least one of the mold 12 and the laser displacement meter 20A with respect to the other, and the same applies to other embodiments to be described below.

By scanning the entire surface of the first surface 12a using the laser displacement meter 20A in this manner, the light reception signals (corresponding to a second detection result of the present invention) of the reflection light LB respectively reflected by the first surface 12a and the second surface 12b, and the light reception signal (corresponding to a first detection result of the present invention) of the reflection light LB reflected respectively at the plurality of positions T of the drug surface 16a in each needle-shaped recess 14 are obtained. Thus, as in the first embodiment, the thickness W of the mold 12 and the height Hb of the plurality of positions T of the drug surface 16a in each needle-shaped recess 14 are obtained, and the height Ht of the plurality of positions T of the drug surface 16a of each needle-shaped recess 14 is obtained on the basis of results thereof. As a result, it is possible to calculate the volume of the drug 16 filled in each needle-shaped recess 14.

In a case where the entire surface of the first surface 12a is scanned by the laser displacement meter 20A, identification of the reflection light LB reflected by the first surface 12a and the second surface 12b and the reflection light LB reflected by the drug surface 16a in each needle-shaped recess 14 is performed. This identification method is not limited to a specific method, and an arbitrary method can be adopted. For example, a method of comparing intensities of the light reception signals of the reflection light LB and performing identification may be adopted. Further, a method of identifying each of the detection unit 32 that detects the reflection light LB reflected by the first surface 12a and the second surface 12b in the laser displacement meter 20A and the detection unit 32 that detects the reflection light LB reflected by the drug surface 16a on the basis of information on a relative position of the laser displacement meter 20A and the mold 12 and design information of the laser displacement meter 20A and the mold 12 may be adopted.

Measurement Device of Third Embodiment

Figure 14:
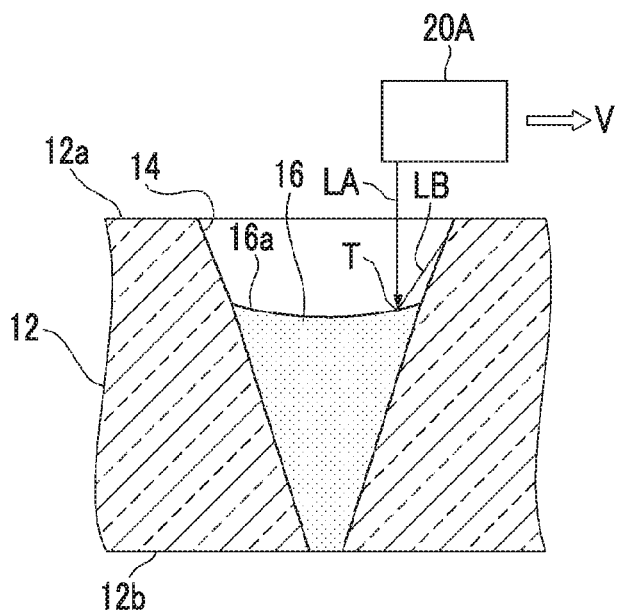
FIG. 14 is an illustrative diagram illustrating a case where reflection light reflected by a drug surface cannot be detected by a detection unit of the laser displacement meter.

FIG. 14 is an illustrative diagram illustrating a case where the reflection light LB reflected by the drug surface 16a cannot be detected by the detection unit 32 of the laser displacement meter 20A (the same applies to the laser displacement meter 20). As illustrated in FIG. 14, in a case where the measurement is performed using the laser displacement meter 20A of a light diffusion, reflection, and reception type which adopts a triangular distance measurement scheme, a wall surface of the needle-shaped recess 14 exists on the optical path of the reflection light LB reflected by the drug surface 16a according to the incidence position of the laser light LA incident on the drug surface 16a in the needle-shaped recess 14 from the laser displacement meter 20A. Therefore, the reflection light LB is blocked or refracted by the wall surface of the needle-shaped recesses 14, and the reflection light LB may be unable to be detected by the detection unit 32.

Figure 15:
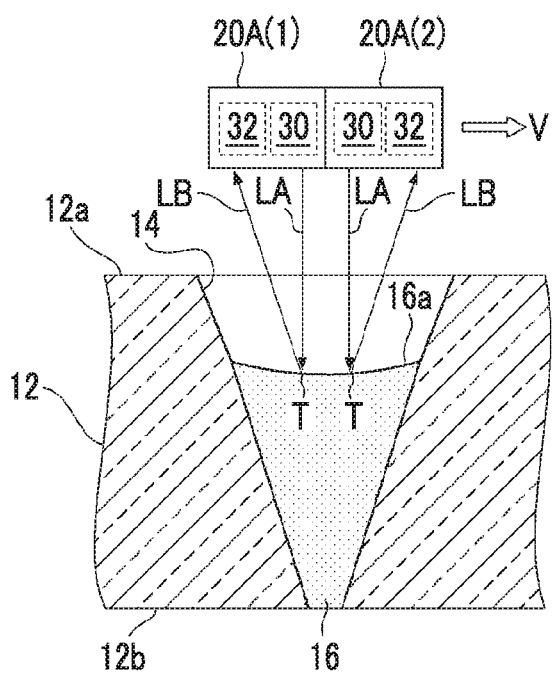
FIG. 15 is an illustrative diagram illustrating detection of a height of a drug surface in each needle-shaped recess of a mold in a measurement device of a third embodiment.

Therefore, as illustrated in FIG. 15, the measurement device 10 of the third embodiment performs the measurement using a plurality of (two, in this example) laser displacement meters 20A(1) and 20A(2). FIG. 15 is an illustrative diagram illustrating detection of heights Hb and Ht of the drug surface 16a in each needle-shaped recess 14 in the measurement device 10 of the third embodiment.

The measurement device 10 of the third embodiment has basically the same configuration as the measurement device 10 in each of the embodiments except that the measurement device 10 of the third embodiment includes two laser displacement meters 20A(1) and 20A(2) in place of the laser displacement meter 20 (see FIG. 1), and components having the same function or configuration as in each of the above embodiments are denoted with the same reference signs and description thereof will be omitted. Further, since the detection of the thickness W of the mold 12 is basically the same as in the first embodiment, specific description thereof will be omitted herein.

The laser displacement meters 20A(1) and 20A(2) are basically the same as the laser displacement meter 20A in a line sensor form described with reference to FIGS. 13A and 13B described above, but positions of the detection units 32 are different. Therefore, the detection unit 32 of each of the laser displacement meters 20A(1) and 20A(2) detects reflection light LB reflected (emitted) in different directions from the drug surface 16a.

In the measurement device 10 of the third embodiment, the laser displacement meters 20A(1) and 20A(2) are relatively moved with respect to the mold 12 by the relative movement unit (not illustrated) in step S15 of FIG. 10 described above. During this relative movement, the laser light LA is incident on the plurality of positions T of the drug surface 16a in each needle-shaped recess 14 from the incidence unit 30 of each of the laser displacement meters 20A(1) and 20A(2).

Further, in the measurement device 10 of the third embodiment, the reflection light LB reflected in different directions from the plurality of positions T according to the incidence of the laser light LA from the incidence unit 30 of each of the laser displacement meters 20A(1) and 20A(2) is detected by the detection unit 32 of each of the laser displacement meters 20A(1) and 20A(2) in step S16 of FIG. 10 described above. That is, at least one of beams of the reflection light LB reflected in two directions at each of the plurality of positions T is reliably detected by at least one of the detection units 32 of the laser displacement meters 20A(1) and 20A(2).

In this example, the beams of laser light LA are individually incident on different positions among a plurality of positions T from the incidence unit 30 of each of the laser displacement meters 20A(1) and 20A(2), but the incidence unit 30 of the laser displacement meters 20A(1) and 20A(2) may be shared. Specifically, the laser light LA vertically incident on one point of the plurality of positions T of the drug surface 16a by the incidence unit 30 is diffused and reflected in a plurality of directions from one point. Thus, the reflection light LB diffused and reflected in a plurality of directions from one point can be individually detected by the detection unit 32 arranged at different positions. Therefore, the incidence unit 30 of each of the laser displacement meters 20A(1) and 20A(2) may be shared, the incidence of the laser light LA on the plurality of positions T of the drug surface 16a from the shared incidence unit 30 may be performed, and the reflection light LB reflected in the plurality of directions from the plurality of positions T according to the incidence may be respectively individually detected by the detection units 32 arranged at different positions.

The laser displacement meter control unit 59 (see FIG. 7) of the third embodiment acquires the light reception signal (corresponding to a first detection result of the present invention) corresponding to the reflection light LB reflected respectively at the plurality of positions T of the drug surface 16a in each needle-shaped recess 14 from the detection unit 32 of each of the laser displacement meters 20A(1) and 20A(2) in step S17 illustrated in FIG. 10 described above. The laser displacement meter control unit 59 outputs the light reception signal of each detection unit 32 to the first height detection unit 61.

The first height detection unit 61 (see FIG. 7) of the third embodiment performs, for each detection unit 32, the detection of the height Hb of the plurality of positions T described above on the basis of, for example, the light reception signal for each detection unit 32 which is input from the laser displacement meter control unit 59 in step S21 illustrated in FIG. 10 described above. Since the method of detecting the height Hb is basically the same as in the first embodiment, specific description thereof will be omitted. The first height detection unit 61 outputs the detection result of the height Hb of each detection unit 32 to the second height detection unit 62.

The second height detection unit 62 (see FIG. 7) of the third embodiment performs, for each detection unit 32, the detection of the height Ht of the plurality of positions T described above on the basis of the detection result of the thickness W of the mold 12 and the detection result of the height Hb of each detection unit 32 input from the first height detection unit 61, in step S22 illustrated in FIG. 10 described above. Since the method of detecting the height Ht is basically the same as in the first embodiment, specific description thereof will be omitted. The second height detection unit 62 outputs the detection result of the height Ht of each detection unit 32 to the volume calculation unit 63.

The volume calculation unit 63 (see FIG. 7) of the third embodiment, first, integrates the detection results of the height Ht of the respective detection units 32 input from the second height detection unit 62, for each needle-shaped recess 14, in step S23 illustrated in FIG. 10 described above.

As described with reference to FIG. 14 described above, the detection unit 32 of each of the laser displacement meters 20A(1) and 20A(2) may be unable to detect the reflection light LB according to incidence positions of the laser light LA incident on the drug surface 16a in the needle-shaped recess 14. However, the detection unit 32 of each of the laser displacement meters 20A(1) and 20A(2) detects the reflection light LB reflected in different directions from the plurality of positions T of the drug surface 16a. Accordingly, at a position at which the reflection light LB cannot be detected by one of the detection units 32 of the laser displacement meters 20A(1) and 20A(2) among the plurality of positions T, the reflection light LB at this position can be detected by the other detection unit 32. Thus, the height Ht of each of the plurality of positions T of the drug surface 16a is reliably obtained from at least one of the detection results of the height Ht of the respective detection units 32 input from the second height detection unit 62. Therefore, by integrating the detection results of the height Ht obtained by the respective detection unit 32 for each needle-shaped recess 14, the height Ht of the plurality of positions T of the drug surface 16a in each needle-shaped recess 14 are obtained.

In a case where the volume calculation unit 63 performs the integration of the detection results of the height Ht, the volume calculation unit 63, for example, first acquires a position at which the reflection light LB cannot be detected by the detection unit 32 of each of the laser displacement meters 20A(1) and 20A(2) among the plurality of positions T of the drug surface 16a in the needle-shaped recesses 14. Such a position at which the reflection light LB cannot be detected is determined for each of the laser displacement meter 20A(1) and 20A(2), the position can be obtained by performing experiment, simulation, or the like in advance.

Next, the volume calculation unit 63 selects a detection result of the height Ht corresponding to the detection unit 32 of the laser displacement meter 20A(2) with respect to a position at which the reflection light LB cannot be detected by the detection unit 32 of the laser displacement meter 20A(1) among the plurality of positions T. Conversely, the volume calculation unit 63 selects a detection result of the height Ht corresponding to the detection unit 32 of the laser displacement meter 20A(1) with respect to a position at which the reflection light LB cannot be detected by the detection unit 32 of the laser displacement meter 20A(2).

On the other hand, the volume calculation unit 63 selects the detection result of the height Ht corresponding to any one of the detection units 32 (which may be an average value of both of the heights Ht) with respect to the position at which both the detection units 32 of the laser displacement meters 20A(1) and 20A(2) can detect the reflection light LB among the plurality of positions T. The volume calculation unit 63 integrates the selected detection results of the height Ht of the respective positions to obtain the heights Ht of the plurality of positions T of the drug surfaces 16a of the needle-shaped recesses 14. A method of integrating the detection result of the height Ht of each detection unit 32 is not limited to the above-described method, and an arbitrary method may be adopted.

The volume calculation unit 63 calculates the volume of the drug 16 filled in each needle-shaped recess 14 on the basis of the integrated height Ht of the plurality of positions T of the drug surface 16a of each needle-shaped recess 14 and the above-described needle-shaped recess shape data 53 (see FIG. 1). Since the method of detecting the volume of the drug 16 in the needle-shaped recesses 14 is basically the same as in the first embodiment, specific description thereof will be omitted. Further, as in the first embodiment, a total volume of the drug 16 in the entire mold 12 may be calculated from the volume of the drug 16 of each needle-shaped recess 14.

Thus, in the measurement device 10 of the third embodiment, it is possible to reliably detect the heights Hb and Ht of the plurality of positions T of the drug surface 16a of each needle-shaped recess 14 by performing the measurement using the plurality of (two in this example) laser displacement meters 20A(1) and 20A(2). As a result, it is possible to obtain the volume of the drug 16 in each needle-shaped recess 14 more accurately.

Although the case where the measurement is performed using the two laser displacement meters 20A(1) and 20A(2) has been described in the measurement device 10 of the third embodiment, the measurement may be performed using three or more laser displacement meters.

Measurement Device of Fourth Embodiment

Figure 16:
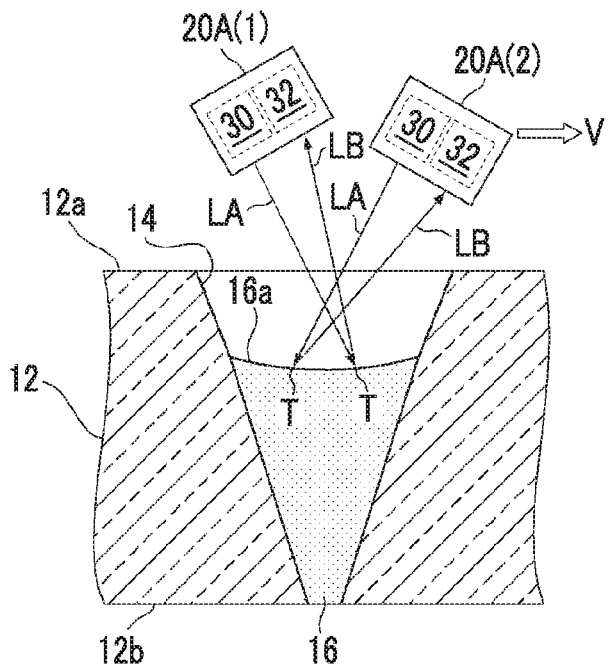
FIG. 16 is a side view of a laser displacement meter of a measurement device of a fourth embodiment.

FIG. 16 is a side view of laser displacement meters 20A(1) and 20A(2) of the measurement device 10 of a fourth embodiment. In the measurement device 10 of the third embodiment, the laser light LA is vertically incident on the plurality of positions T of the drug surface 16a in the needle-shaped recess 14 from the incidence unit 30 of each of the laser displacement meters 20A(1) and 20A(2) in step S15 illustrated in FIG. 10 described above, but the present invention is not necessarily limited to the vertical incidence.

Specifically, the laser light LA may be obliquely incident on the plurality of positions T of the drug surface 16a in the needle-shaped recess 14 from a plurality of directions by the incidence unit 30 of each of the laser displacement meters 20A(1) and 20A(2), as illustrated in FIG. 16. The measurement device 10 of the fourth embodiment has basically the same configuration as the measurement device 10 of the third embodiment except that the laser displacement meters 20A(1) and 20A(2) are inclined, and components having the same function or configuration as in each of the above embodiments are denoted with the same reference signs and description thereof will be omitted.

In the measurement device 10 of the fourth embodiment, in steps S15 and S16 illustrated in FIG. 10 described above, reflection light LB reflected from the plurality of positions T of the drug surface 16a in each needle-shaped recess 14 is detected by each detection unit 32 of the laser displacement meters 20A(1) and 20A(2), similar to the third embodiment. Further, the laser displacement meter control unit 59 (see FIG. 7) acquires the light reception signal of the reflection light LB from the detection unit 32 of each of the laser displacement meters 20A(1) and 20A(2) and outputs the light reception signal of each detection unit 32 to the first height detection unit 61 in step S17 illustrated in FIG. 10 described above.

The first height detection unit 61 (see FIG. 7) of the fourth embodiment performs, for each detection unit 32, detection of the height Hb of the plurality of positions T of the drug surface 16a in each needle-shaped recess 14 on the basis of, for example, the light reception signal of each detection unit 32 which is input from the laser displacement meter control unit 59 in step S21 illustrated in FIG. 10 described above.

Figure 17:
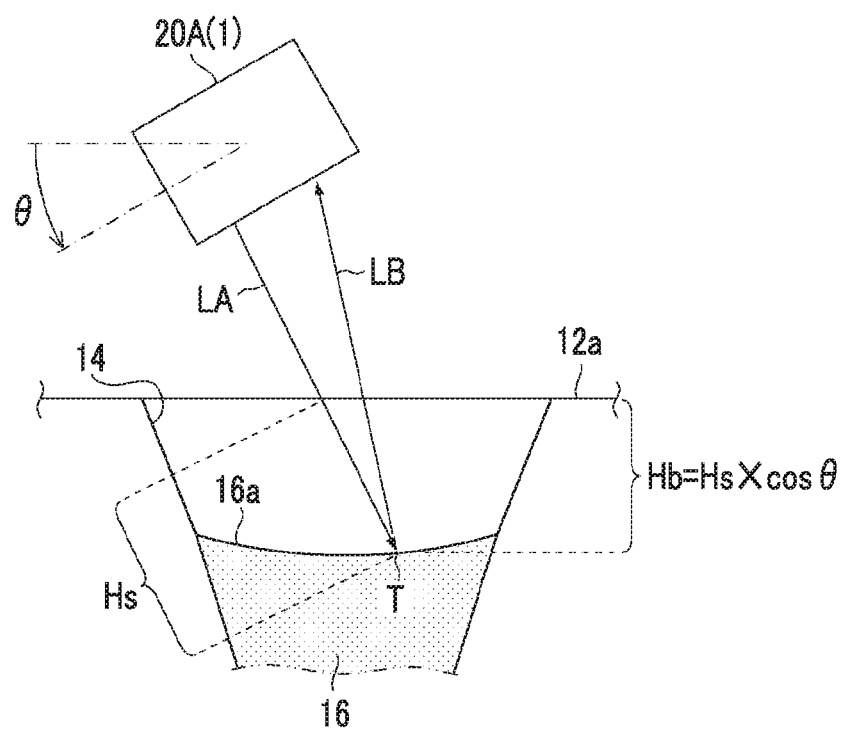
FIG. 17 is an illustrative diagram illustrating a process of detecting a height of a plurality of positions on a drug surface in a needle-shaped recess in a first height detection unit of the fourth embodiment.

FIG. 17 is an illustrative diagram illustrating a process of detecting the height Hb at the plurality of positions T in the first height detection unit 61 of the fourth embodiment. As illustrated in FIG. 17, a height that is detected in a case where oblique incidence of the laser light LA on the plurality of positions T from the incidence unit 30 of the laser displacement meter 20A(1) [the laser displacement meter 20A(2) is not illustrated] is performed becomes a height Hs illustrated in FIG. 17. Therefore, the first height detection unit 61 detects, for each detection unit 32, the height Hs at the plurality of positions T of the drug surface 16a in each needle-shaped recess 14 on the basis of the light reception signal or the like for each detection unit 32 which is input from the laser displacement meter control unit 59.

Then, the first height detection unit 61 detects, for each detection unit 32, the height Hb of the plurality of positions T of the drug surface 16a in each needle-shaped recess 14 from a result of the detection of the height Hs of each detection unit 32 and an inclination angle θ of each of the laser displacement meters 20A(1) and 20A(2). Specifically, the first height detection unit 61 calculates the height Hb from the height Hs and inclination angle θ using a formula Hb=Hs×cos θ. The inclination angle θ is an inclination angle with respect to a posture in a case where the laser displacement meters 20A(1) and 20A(2) perform the vertical incidence of the laser light LA on the drug surface 16a or the first surface 12a. Thus, in the first height detection unit 61 of the fourth embodiment, it is possible to detect the height Hb of the plurality of positions T of the drug surface 16a in each needle-shaped recess 14 in each detection unit 32.

In a case where the thickness acquisition unit 60 of the fourth embodiment detects the thickness W of the mold 12, the thickness acquisition unit 60 detects the thickness W of the mold 12 from the thickness (not illustrated) in a diagonal direction of the mold 12 obtained from the light reception signals respectively corresponding to the reflection light LB on the first surface 12a and the reflection light LB on the second surface 12b and the above-descried inclination angle θ, like the detection of the height Hb described above.

Since a process after detection of the height Hb of each detection unit 32 in the first height detection unit 61 is basically the same as in the third embodiment described above, specific description thereof will be omitted.

Thus, in the measurement device 10 of the fourth embodiment, the heights Hb and Ht of the plurality of positions T of the drug surfaces 16a of the respective needle-shaped recesses 14 can be reliably detected by performing measurement using a plurality of (two in this example) laser displacement meters 20A (1) and 20A(2). As a result, it is possible to obtain the volume of the drug 16 in each needle-shaped recess 14 more accurately.

Figure 18:
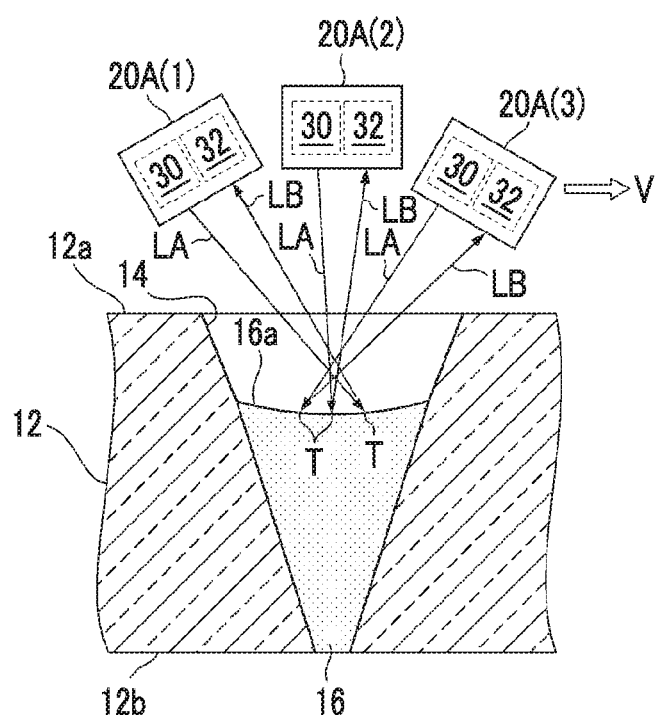
FIG. 18 is an illustrative diagram illustrating a modification example of the fourth embodiment in which the measurement of the volume of the drug in each needle-shaped recess is performed using three laser displacement meters.

Although the measurement of the volume of the drug 16 in the needle-shaped recess 14 is performed using the two laser displacement meters 20A(1) and 20A(2) in the fourth embodiment, the number of laser displacement meters may be increased to three or more and the measurement may be performed. For example, the laser light LA is incident on the drug surface 16a or the first surface 12a from a plurality of directions by the respective incidence units 30 of the three laser displacement meters 20A(1), 20A(2), and 20A(3) as illustrated in FIG. 18, and therefore, the volume of the drug 16 in the needle-shaped recess 14 can be measured, as in the fourth embodiment. FIG. 18 is a diagram illustrating a modification example of the fourth embodiment in which the measurement of the volume of the drug 16 in the needle-shaped recess 14 is performed using the three laser displacement meters 20A(1) to 20A(3).

Measurement Device of Fifth Embodiment

Figure 19:
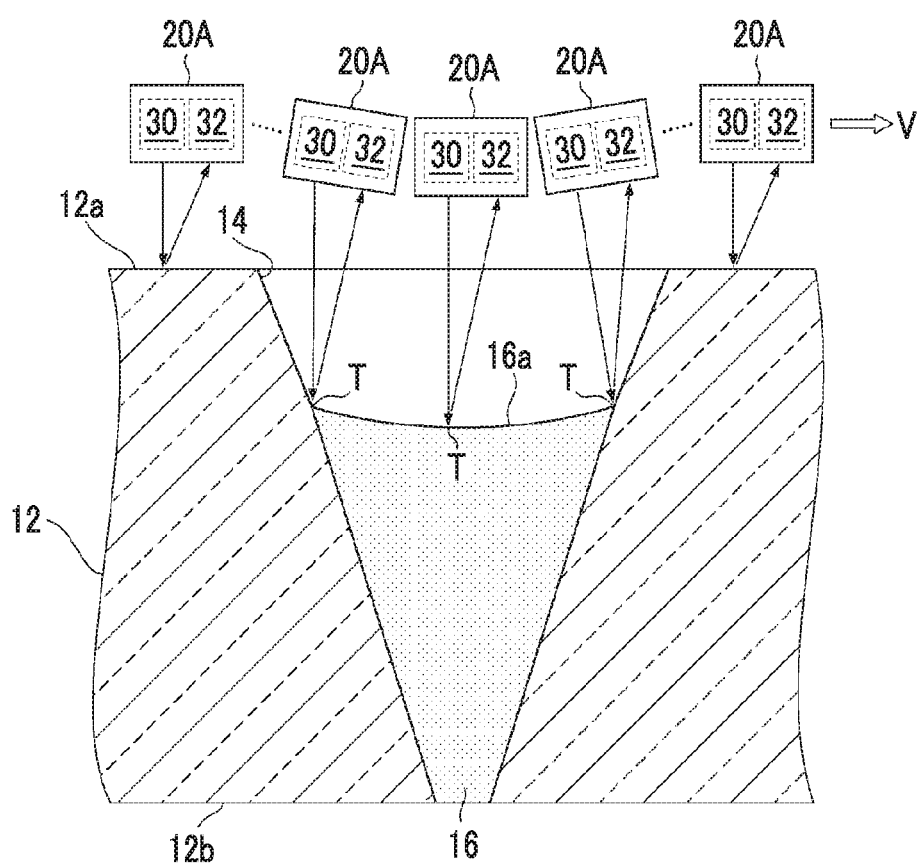
FIG. 19 is an illustrative diagram illustrating a measurement method in a measurement device of a fifth embodiment.

FIG. 19 is an illustrative diagram illustrating a measurement method in the measurement device 10 of a fifth embodiment. In the third and fourth embodiments, the measurement is performed using, for example, two laser displacement meters 20A(1) and 20A(2) in consideration of a case where the reflection light LB cannot be detected by the detection unit 32 according to the incidence position of the laser light LA as described with reference to FIG. 14 described above. On the other hand, in the measurement device 10 of the fifth embodiment, the same effects as those of the third and fourth embodiments are obtained through measurement using one laser displacement meter 20A.

Since the measurement device 10 of the fifth embodiment has basically the same configuration as the measurement device 10 of the second embodiment, components having the same function or configuration as in each of the above embodiments are denoted with the same reference signs and description thereof will be omitted.

As illustrated in FIG. 19, in the measurement device 10 of the fifth embodiment, the incidence of the laser light LA by the incidence unit 30 and the detection of the reflection light LB by each detection unit 32 are executed while relatively moving the laser displacement meter 20A with respect to the mold 12 using the relative movement unit (not illustrated), similar to the measurement device 10 of the second embodiment described above, in step S15 of FIG. 10 described above. Thus, the laser light LA is sequentially incident on the plurality of positions (the first surface 12a or the drug surface 16a in each needle-shaped recess 14) of the mold 12 from the incidence unit 30 of the laser displacement meter 20A, and the reflection light LB sequentially reflected at the plurality of positions can be detected by the detection unit 32.

In this case, in the fifth embodiment, the incidence of the laser light LA at the incidence angle determined in advance for every plurality of positions T on the plurality of positions T of the drug surface 16a in each needle-shaped recess 14 from the incidence unit 30 of the laser displacement meter 20A is performed. Further, in the fifth embodiment, the reflection light LB reflected by the plurality of positions T according to the incidence of the laser light LA is detected by the detection unit 32. Although the number of the plurality of positions T is set to three in order to prevent complication of the drawing, the number may be four or more.

Here, the incidence angle determined in advance for every plurality of positions T is, for example, an incidence angle at which the laser light LA is substantially vertically incident on each of the plurality of positions T according to a shape of the drug surface 16a that is an arc shape (an arc shape that is convex from the first surface 12a to the second surface 12b, or an arc shape that is convex from the second surface 12b to the first surface 12a). The incidence angle of the laser light LA with respect to each of a plurality of positions T is not particularly limited as long as the incidence angle is an angle at which the detection unit 32 can detect the reflection light LB reflected at each of the plurality of positions T, and is determined by performing experiment, simulation, or the like in advance.

The position of the laser displacement meter 20A (the incidence unit 30) when the laser light LA is incident on each of the plurality of positions T, and the posture (inclination) of the laser displacement meter 20A are adjusted on the basis of such an incidence angle determined in advance for every plurality of positions T. The posture of the laser displacement meter 20A is adjusted by a posture adjustment unit (not illustrated). Thus, the laser light LA can be incident on the plurality of positions T of the drug surface 16a in each needle-shaped recess 14 at the incidence angle predetermined in advance for every plurality of positions T from the incidence unit 30 of the laser displacement meter 20A which is relatively moved with respect to the mold 12. Further, the reflection light LB from the plurality of positions T according to the incidence of the laser light LA can be detected by the detection unit 32.

The laser displacement meter control unit 59 of the fifth embodiment (see FIG. 7) acquires the light reception signals (a second detection result of the present invention) corresponding to the reflection light LB reflected by the first surface 12a and the second surface 12b of the mold 12 from the detection unit 32 of the laser displacement meter 20A in step S13 illustrated in FIG. 10 described above, and outputs the acquired light reception signal to the thickness acquisition unit 60 (see FIG. 7). Thus, the thickness W of the mold 12 is detected by the thickness acquisition unit 60, and the detection result of the thickness W is output to the second height detection unit 62, as in the first embodiment. The thickness W of the mold 12 may be acquired from the thickness information 64 in the storage unit 47 illustrated in FIG. 1 described above.

Further, the laser displacement meter control unit 59 of the fifth embodiment acquires the light reception signals (a first detection result of the present invention) corresponding to the reflection light LB reflected at the plurality of positions T of the drug surface 16a in each needle-shaped recess 14 from the detection unit 32 of the laser displacement meter 20A and outputs the acquired light reception signal to the first height detection unit 61 in step S17 illustrated in FIG. 10 described above.

The first height detection unit 61 (see FIG. 7) of the fifth embodiment performs detection of the height Hb of the plurality of positions T of the drug surface 16a in each needle-shaped recess 14 on the basis of the light reception signal input from the laser displacement meter control unit 59 in step S21 illustrated in FIG. 10 described above. In this case, in a case where the first height detection unit 61 detects the height Hb of the position at which the laser light LA is not vertically incident among the plurality of positions T (that is, a position at which the laser light LA is obliquely incident), the first height detection unit 61 performs the detection of the height Hb using the method described with reference to FIG. 17 of the fourth embodiment described above. Thus, it is possible to detect the height Hb of the plurality of positions T of the drug surface 16a in each needle-shaped recess 14.

Since a process after the detection of the height Hb of the first height detection unit 61 is basically the same as in the first embodiment, specific description thereof will be omitted.

Thus, in the measurement device 10 of the fifth embodiment, it is possible to reliably detect the heights Hb and Ht of the plurality of positions T of the drug surface 16a of each needle-shaped recess 14, similar to the third embodiment or the fourth embodiment described above, by causing the laser light LA to be incident on the plurality of positions T of the drug surface 16a in each needle-shaped recess 14 at an incidence angle determined in advance for every plurality of positions T from the incidence unit 30 of the laser displacement meter 20A while relatively moving the laser displacement meter 20A with respect to the mold 12. As a result, it is possible to obtain the volume of the drug 16 in each needle-shaped recess 14 more accurately.

Measurement Device of Sixth Embodiment

Figure 20A:
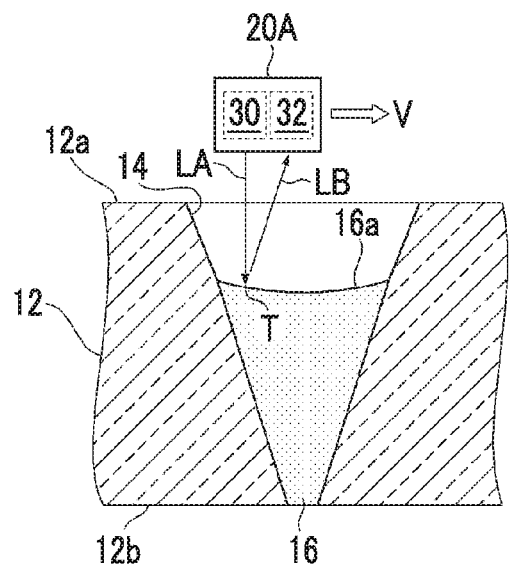
FIGS. 20A and 20B are illustrative diagrams illustrating measurement in a measurement device 10 of a sixth embodiment.
Figure 20B:
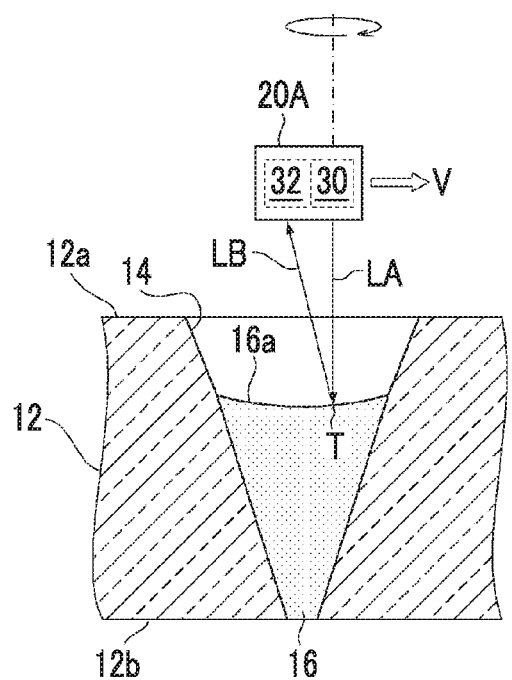

FIGS. 20A and 20B are illustrative diagrams illustrating measurement in the measurement device 10 of a sixth embodiment. The measurement device 10 of the sixth embodiment achieves the same effects as in the third and fourth embodiments through measurement using one laser displacement meter 20A, similar to the fifth embodiment. Since the measurement device 10 of the sixth embodiment has basically the same configuration as the measurement device 10 of the second embodiment, components having the same function or configuration as in each of the above embodiments are denoted with the same reference signs and description thereof will be omitted.

As illustrated in FIGS. 20A and 20B, the measurement device 10 of the sixth embodiment executes incidence of the laser light LA in the incidence unit 30 and detection of the reflection light LB in the detection unit 32 while relatively moving the laser displacement meter 20A with respect to the mold 12 using a relative movement unit (not illustrated), similar to the second embodiment described above, in step S15 of FIG. 10 described above. Thus, it is possible to cause the laser light LA to be incident on the plurality of positions T of the drug surface 16a in each needle-shaped recess 14 from the incidence unit 30 of the laser displacement meter 20A, and detect the reflection light LB reflected respectively at the plurality of positions T using the detection unit 32.

In this case, in the sixth embodiment, in a case where the reflection light LB reflected from the plurality of positions T is detected by the detection unit 32, the reflection light LB reflected in a predetermined direction at the plurality of positions T is detected by the detection units 32. Here, the "predetermined direction" may be a direction in which the reflection light LB is not blocked or refracted by a wall surface or the like of the needle-shaped recess 14 as illustrated in FIG. 14 described above, that is, a reflection direction in which the detection unit 32 can detect the reflection light LB, and is determined by performing experiment, simulation, or the like in advance.

For example, in the sixth embodiment, any one of the reflection direction of the reflection light LB illustrated in FIG. 20A or the reflection direction of the reflection light LB illustrated in FIG. 20B is set as the "predetermined direction" for every plurality of positions T. The "predetermined direction" is not particularly limited to the direction illustrated in FIGS. 20A and 20B.

Further, in the sixth embodiment, the laser displacement meter 20A can be rotated about an axis perpendicular to the first surface 12a and the second surface 12b by a rotation unit (not illustrated). Thus, by rotating the laser displacement meter 20A using the rotation unit, the detection unit 32 can selectively detect the reflection light LB reflected in the reflection direction illustrated in FIG. 20A and the reflection light LB reflected in the reflection direction illustrated in FIG. 20B. Thus, by performing rotation control of the laser displacement meter 20A in the rotation unit described above on the basis of the result of setting of the "predetermined direction" of every plurality of positions T, the detection unit 32 can detect the reflection light LB detected in the direction determined in advance for every plurality of positions T. That is, the reflection light LB reflected respectively at the plurality of positions T can be reliably detected by the detection unit 32.

The mold 12 (for example, the stage 19 illustrated in FIG. 1) may be rotated instead of rotating the laser displacement meter 20A about a vertical axis described above.

The laser displacement meter control unit 59 of the sixth embodiment acquires the light reception signal (corresponding to a first detection result of the present invention) corresponding to the reflection light LB reflected respectively at the plurality of positions T of the drug surface 16a in each needle-shaped recess 14 from each detection unit 32 of the laser displacement meter 20A, and outputs the acquired light reception light signal to the first height detection unit 61 in step S17 illustrated in FIG. 10 described above. Since subsequent processes are basically the same as in the first embodiment, specific description thereof will be omitted.

Thus, in the measurement device 10 of the sixth embodiment, since the detection unit 32 detects the reflection light LB reflected in a predetermined direction from the plurality of positions T while relatively moving the laser displacement meter 20A with respect to the mold 12, the reflection light LB from the plurality of positions T is reliably detected by the detection unit 32 without being blocked or refracted by a wall surface of the needle-shaped recesses 14 or the like. As a result, the heights Hb and Ht of the plurality of positions T of the drug surface 16a of each needle-shaped recess 14 can be reliably detected, and therefore, it is possible to more accurately obtain the volume of the drug 16 in each needle-shaped recess 14, as in the third to fifth embodiment described above.

Measurement Device of Seventh Embodiment

Figure 21A:
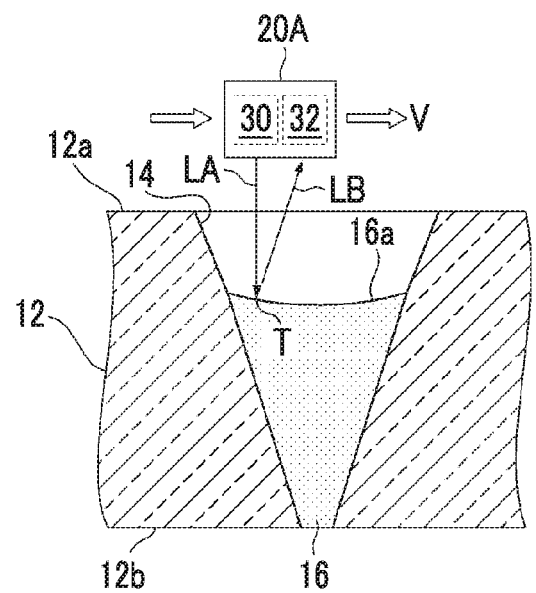
FIGS. 21A and 21B are illustrative diagrams illustrating measurement in a measurement device 10 of a seventh embodiment.
Figure 21B:
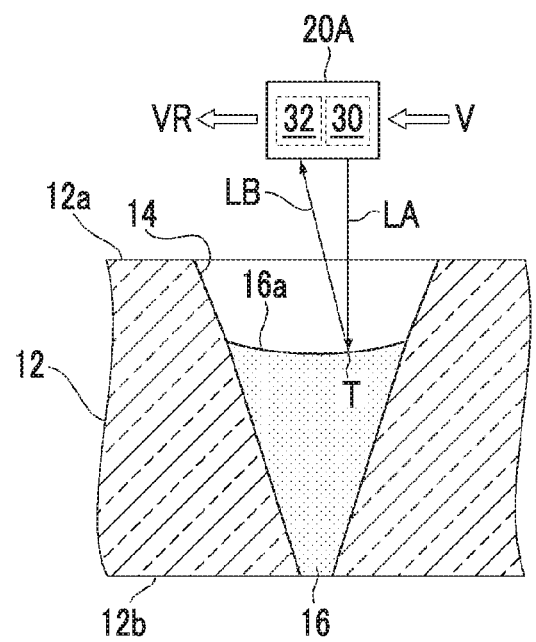

FIGS. 21A and 21B are illustrative diagrams illustrating the measurement in the measurement device 10 of a seventh embodiment. In the sixth embodiment, scanning in which the laser light LA is incident on the plurality of positions T of the drug surface 16a in each needle-shaped recess 14 from the incidence unit 30 while relatively moving the laser displacement meter 20A with respect to the mold 12 is performed once, whereas this scanning is performed in a plurality of times in the measurement device 10 of the seventh embodiment. Since the measurement device 10 of the seventh embodiment has basically the same configuration as the measurement device 10 of the second embodiment or the sixth embodiment, components having the same function or configuration as in each of the above embodiments are denoted with the same reference signs and description thereof will be omitted.

As illustrated in FIG. 21A, in the measurement device 10 of the seventh embodiment, the incidence of the laser light LA by the incidence unit 30 and the detection of the reflection light LB by the detection unit 32 are executed while relatively moving the laser displacement meter 20A in a direction indicated by an arrow V with respect to the mold 12 using a relative movement unit (not illustrated) in step S15 of FIG. 10 described above, similar to the second embodiment. Through the first scan, the laser light LA is incident on the plurality of positions T of the drug surface 16a in each needle-shaped recess 14 from the incidence unit 30 of the laser displacement meter 20A, and the reflection light LB reflected at the plurality of positions T can be detected by the detection unit 32.

As illustrated in FIG. 21B, after the first scan is completed, the laser displacement meter 20A is rotated about an axis perpendicular to the first surface 12a and the second surface 12b by the rotation unit (not illustrated). Then, the incidence of the laser light LA by the incidence unit 30 and the detection of the reflection light LB by the detection unit 32 are executed again while relatively moving the laser displacement meter 20A in a direction indicated by an arrow VR with respect to the mold 12 by the relative movement unit (not illustrated). Through the second scan, the laser light LA can be incident on the plurality of positions T of the drug surface 16a in each needle-shaped recess 14 from the incidence unit 30 of the laser displacement meter 20A, and the reflection light LB reflected at the plurality of positions T can be detected by the detection unit 32.

Thus, in the first scan and the second scan, the reflection light LB reflected in different directions at the plurality of positions T is detected by the detection unit 32. That is, the reflection light LB reflected (emitted) in different directions for each scan from the plurality of positions T can be detected for each scan by the detection unit 32. Thus, the reflection light LB reflected from each of the plurality of positions T can be reliably detected at least one of the two scans for the same reason as in the third embodiment.

The mold 12 (for example, the stage 19 illustrated in FIG. 1) may be rotated instead of the laser displacement meter 20A being rotated about the above-described vertical axis. Further, the rotation angle when at least one of the laser displacement meter 20A and the mold 12 is relatively rotated with respect to the other is not particularly limited, but it is preferable for the rotation angle to be determined by performing experiment, simulation, or the like in advance so that the reflection light LB reflected from each of the plurality of positions T can be reliably detected.

The laser displacement meter control unit 59 (see FIG. 7) of the seventh embodiment acquires, for each scan, the light reception signal (corresponding to a first detection result of the present invention) corresponding to the reflection light LB reflected respectively at the plurality of positions T of the drug surface 16a in each needle-shaped recess 14 from the detection unit 32 of the laser displacement meter 20A in step S17 illustrated in FIG. 10 described above. The laser displacement meter control unit 59 outputs the light reception signal for each scan to the first height detection unit 61.

The first height detection unit 61 (see FIG. 7) of the seventh embodiment performs, for each scan, detection of the height Hb of the plurality of positions T described above on the basis of the light reception signal for each scan input from the laser displacement meter control unit 59, or the like in step S21 illustrated in FIG. 10 described above. The first height detection unit 61 outputs the detection result of the height Hb for each scan to the second height detection unit 62.

The second height detection unit 62 (see FIG. 7) of the seventh embodiment performs, for each scan, detection of the height Ht of the plurality of positions T described above on the basis of the detection result of the thickness W of the mold 12 and the detection result of the height Hb for each scan input from the first height detection unit 61 in step S22 illustrated in FIG. 10 described above. The second height detection unit 62 outputs the detection result of the height Ht for each scan to the volume calculation unit 63.

The volume calculation unit 63 (see FIG. 7) of the seventh embodiment integrates the detection result of the height Ht of each scan input from the second height detection unit 62, for each needle-shaped recess 14 using basically the same method as in the third embodiment in step S23 illustrated in FIG. 10 described above. The volume calculation unit 63 calculates the volume of the drug 16 in each needle-shaped recess 14 on the basis of the integrated height Ht of the plurality of positions T of the drug surface 16a of each needle-shaped recess 14, and the needle-shaped recess shape data 53 described above. Since subsequent processes are the same as in the third embodiment, description thereof will be omitted.

Thus, in the measurement device 10 of the seventh embodiment, since scans of the laser displacement meter 20A are performed a plurality of times and the reflection light LB emitted in a different direction in each scan is detected, it is possible to reliably detect the heights Hb and Ht of the plurality of positions T of the drug surface 16a of each needle-shaped recess 14, as in the third embodiment, or the like. As a result, it is possible to obtain the volume of the drug 16 in each needle-shaped recess 14 more accurately.

Although scanning using the laser displacement meter 20A is performed twice in the seventh embodiment, the scanning is performed three or more times and the reflection light LB emitted in different directions may be detected for each scan.

Measurement Device of Eighth Embodiment

Figure 22:
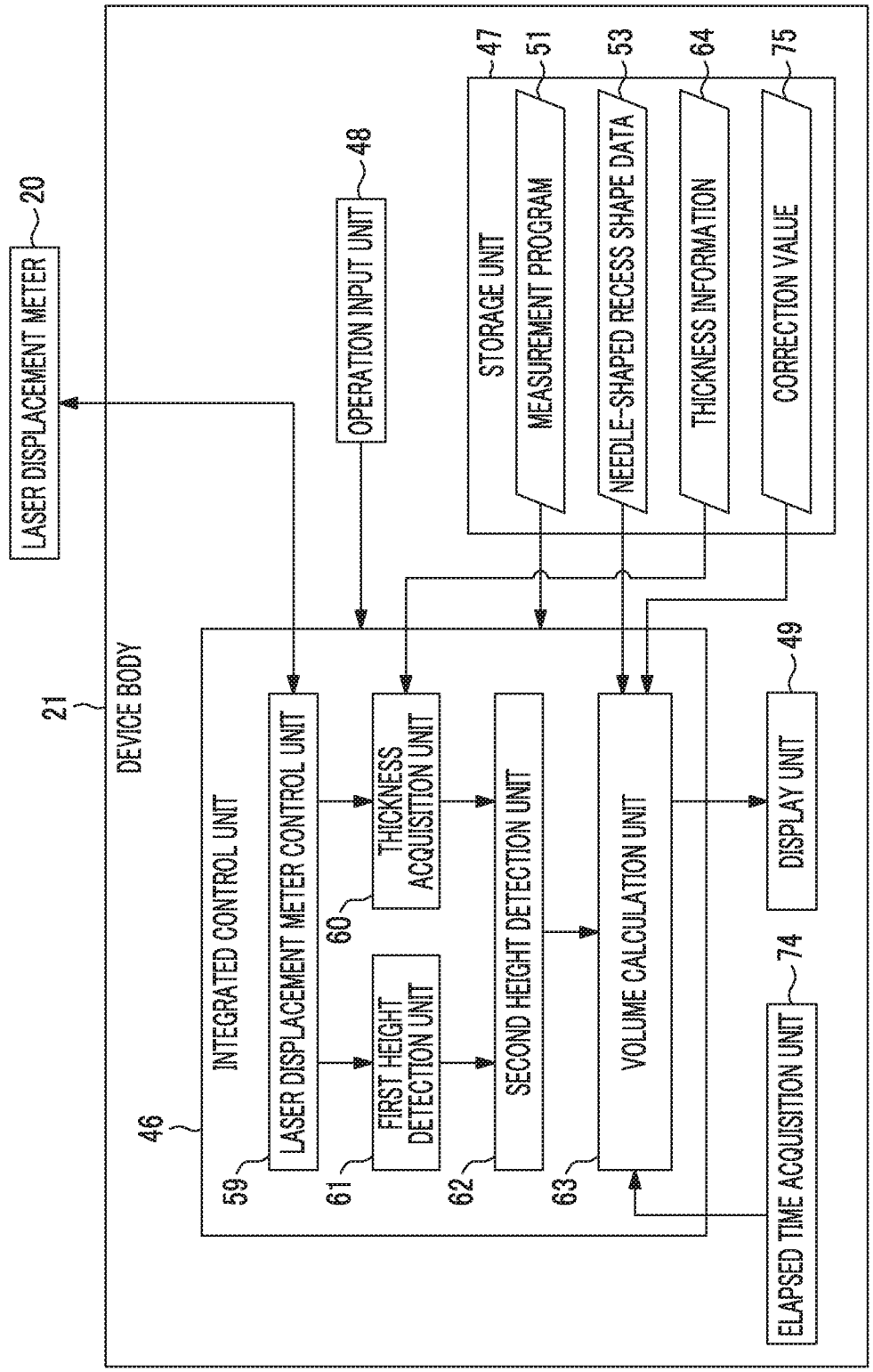
FIG. 22 is a block diagram illustrating a configuration of a measurement device according to an eighth embodiment.

FIG. 22 is a block diagram illustrating a configuration of a measurement device 10 of an eighth embodiment. In each of the above embodiments, the volume of the drug 16 in the needle-shaped recesses 14 is calculated, but since the water contained in the drug 16 filled in each needle-shaped recess 14 evaporates with the lapse of time as described above, the volume of the drug 16 in each needle-shaped recess 14 decreases with the lapse of time from the time of the filling (see FIGS. 3A through 3C and 9). Therefore, in the measurement device 10 of the eighth embodiment, the amount of filling of the drug 16 filled in each needle-shaped recess 14 (the volume immediately after filling of the drug 16) is calculated. The measurement device 10 of the eighth embodiment has basically the same configuration as the measurement device 10 in each of the above embodiments except that the amount of filling of the drug 16 filled in each needle-shaped recess 14 is calculated, and components having the same function or configuration as in each of the above embodiments are denoted with the same reference signs and description thereof will be omitted.

As illustrated in FIG. 22, the elapsed time acquisition unit 74 is provided in the device body 21 of the measurement device 10 of the eighth embodiment, and the correction value 75 is stored in the storage unit 47.

The elapsed time acquisition unit 74 acquires the elapsed time until step S15 illustrated in FIG. 10 described above [a first incidence step (detection result acquisition step) of the present invention] starts after the drug 16 is filled in each needle-shaped recess 14. For example, the elapsed time acquisition unit 74 compares a filling time of the drug 16 in the needle-shaped recess 14 that has been input in advance with the start time of the step S15 described above to acquire the above-described elapsed time. The elapsed time acquisition unit 74 outputs the acquired elapsed time to the volume calculation unit 63.

The correction value 75 is a correction value for correcting a decrease over time in the volume of the drug 16 filled in each needle-shaped recess 14 and is obtained, for example, for each elapsed time, from the graph showing a temporal change in the volume of the drug 16 filled in the needle-shaped recess 14 as illustrated in FIG. 9 described above.

Specifically, since the amount of decrease in the drug 16 per elapsed time is determined from the graph illustrated in FIG. 9, the amount of the decrease in the drug 16 per elapsed time can be used as the correction value 75. Since a one-to-one relationship is held between the volume of the drug 16 in the needle-shaped recess 14 and the known height Ht (see FIG. 4), "correcting a decrease over time in the volume of the drug 16" described above includes "correcting a decrease over time in the height Vt of the drug 16". Accordingly, the correction value 75 includes a correction value for indirectly correcting the volume of the drug 16 in the needle-shaped recess 14 by correcting the height Ht of the drug 16 in the needle-shaped recess 14 with the height Ht at the time of filling, in addition to the correction value for directly correcting the volume of the drug 16 in the needle-shaped recess 14.

The volume calculation unit 63 of the measurement device 10 of the eighth embodiment calculates the amount of filling of the drug 16 filled in each needle-shaped recess 14 on the basis of the elapsed time input from the elapsed time acquisition unit 74 and the correction value 75 read from the storage unit 47, in addition to the calculation of the volume of the drug 16 in the needle-shaped recess 14 as in the first embodiment.

Figure 23:
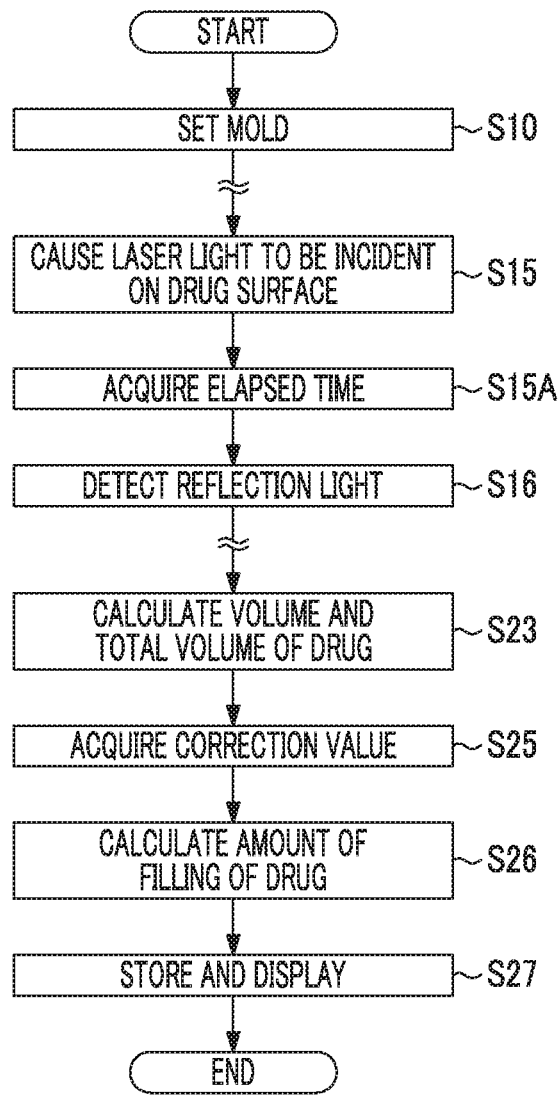
FIG. 23 is a flowchart illustrating a flow of measurement of the amount of filling of a drug filled in each needle-shaped recess in the measurement device of the eighth embodiment.

FIG. 23 is a flowchart illustrating a flow of measurement of the amount of filling of the drug 16 filled in each needle-shaped recess 14 in the measurement device 10 of the eighth embodiment. As illustrated in FIG. 23, the flow of processing up to step S23 is basically the same as in the first embodiment illustrated in FIG. 10 described above. However, in the eighth embodiment, after the process of step S15, the elapsed time acquisition unit 74 acquires the above-described elapsed time and outputs the acquired elapsed time to the volume calculation unit 63 (step S15A, which corresponds to an elapsed time acquisition step of the present invention).

The volume calculation unit 63 of the eighth embodiment obtains, for example, the volume of the drug 16 of each needle-shaped recess 14 as in the first embodiment in step S23, and then, acquires the correction value 75 from the storage unit 47 (step S25, which corresponds to the correction value acquisition step of the present invention).

Then, the volume calculation unit 63 corrects the volume of the drug 16 for each needle-shaped recess 14 with the correction value 75 corresponding to the elapsed time on the basis of the elapsed time acquired by the elapsed time acquisition unit 74. For example, the volume calculation unit 63 adds a decrease amount (correction value 75) of the drug 16 according to the elapsed time to the volume of the drug 16 for each needle-shaped recess 14. Accordingly, the filling amount of the drug 16 filled in each needle-shaped recess 14 is calculated (step S26).

In a case where the correction value 75 is a correction value of the above-described height Ht, the volume calculation unit 63 corrects the detection result of the height Ht of each needle-shaped recess 14 which is input from the second height detection unit 62 with the correction value 75, and calculates the height Ht immediately after filling of the drug 16 in the needle-shaped recesses 14. Accordingly, it is possible to indirectly correct the volume of the drug 16 for each needle-shaped recess 14. The volume calculation unit 63 calculates the amount of filling of the drug 16 filled in the needle-shaped recess 14 on the basis of the height Ht of the drug 16 at the plurality of positions T immediately after the filling in each needle-shaped recess 14 and the needle-shaped recess shape data 53 read from the storage unit 47.

Further, in a case where the volume calculation unit 63 has calculated the amount of filling of the drug 16 of each needle-shaped recess 14, the volume calculation unit 63 calculates the total volume of the amount of filling of the drug 16 in the entire mold 12 from the filling amount of the drug 16 of each needle-shaped recess 14.

The volume calculation unit 63 outputs the calculation result of the volume and the total volume of the drug 16 of each needle-shaped recess 14 and the calculation result of the total volume of each of the volume and the amount of filling of the drug 16 to the storage unit 47 and the display unit 49. Thus, the calculation result of the volume and the total volume of the drug 16 of each needle-shaped recess 14 is stored in the storage unit 47 as a measurement result of the volume and the amount of filling of the drug 16 of each needle-shaped recess 14, and is displayed on the display unit 49 (step S27). Further, the calculation result of the total volume of each of the volume and the amount of filling of the drug 16 is stored in the storage unit 47 as a measurement result of the total volume of each of the volume and the amount of filling of the drug 16, and is displayed on the display unit 49 (step S27).

Further, on the display unit 49, an allowable criterion of the volume of the drug 16, an allowable criterion of the amount of filling, and an allowable criterion of a total volume of each of the volume and the amount of filling are displayed, and a determination result obtained by determining whether or not each satisfies the allowable criterion is displayed.

Thus, in the measurement device 10 of the eighth embodiment, since the amount of filling of the drug 16 filled in the needle-shaped recess 14 can be measured, a result of the measurement can be fed back to a filling device (not illustrated) that fills the drug 16 in the needle-shaped recess 14 of the mold 12. As a result, it is possible to appropriately adjust the amount of filling of the drug 16 for each needle-shaped recess 14 in the filling device.

Modification Examples of Second to Eighth Embodiments

In the second to eighth embodiments, the addition of the dye 70 (see FIG. 11), the hydrophilic process for the first surface 12*a* (see FIG. 12), the use of various types of laser displacement meters, performance of a modification example of a method of detecting the thickness W of the mold 12, use of an optical measurement device other than the laser displacement meter, and the like may be performed, similar to the modification example of the first embodiment described above. Further, the measurement device 10 of the second to eighth embodiments may include only the device body 21. Further, the number of communication holes 31 formed in each needle-shaped recess 14 on the second surface 12*b* of the mold 12, and a size of a diameter may be changed.

[Others]

Although the case where the first surface 12*a* of the mold 12 is the reference surface of the present invention and the thickness W of the mold 12 is the reference surface height of the present invention has been described in each of the above embodiments, an arbitrary surface parallel to the first surface 12*a* or the second surface 12*b* (including parallel to both) may be changed as the reference surface, and the reference surface height may be changed according to the change in the reference surface. Here, parallel includes substantially parallel.

Figure 24:
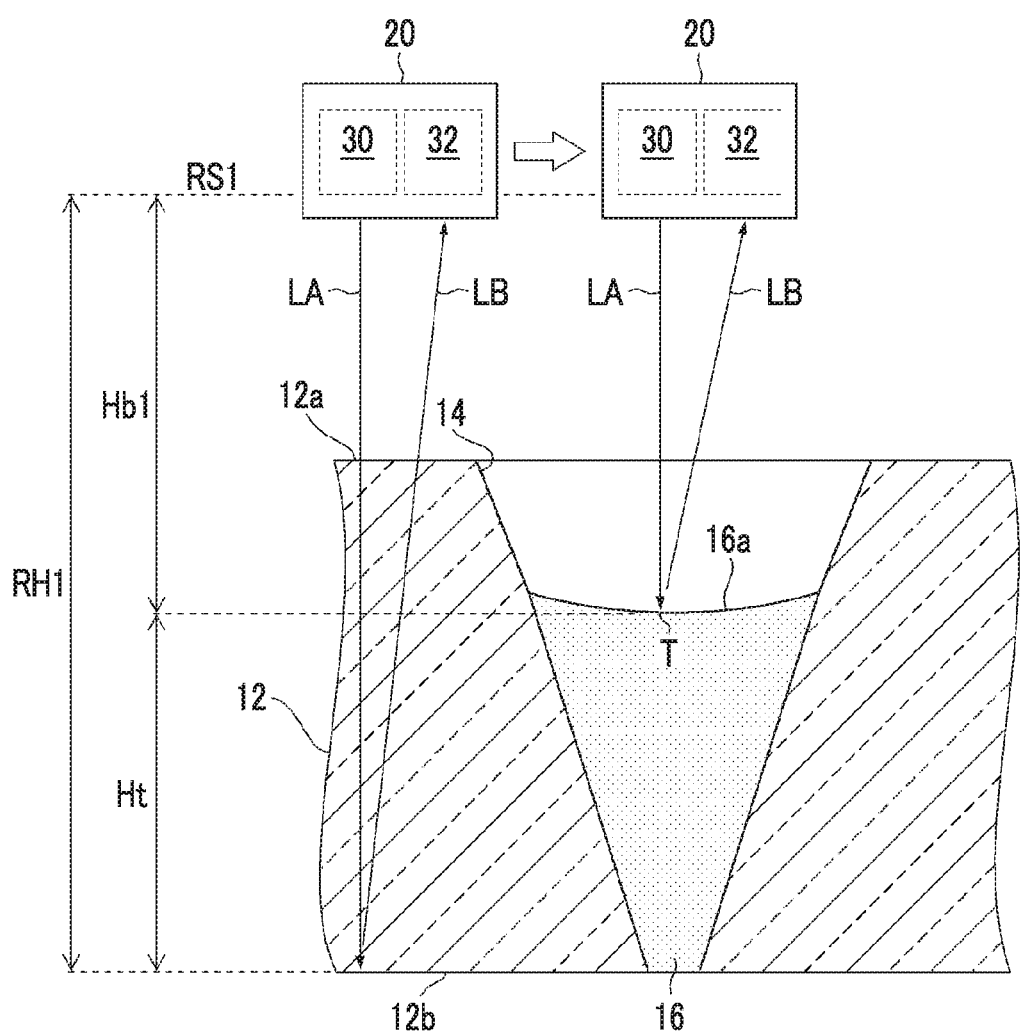
FIG. 24 is an illustrative diagram illustrating a process of detecting a height Ht in a case where a plane at the same height as that of a detection unit of a laser displacement meter is set as a reference surface.

FIG. 24 is an illustrative diagram illustrating a process of detecting the height Ht in a case where a plane at the same height (including substantially the same height) as that of the detection unit 32 of the laser displacement meter 20 is set as the reference surface RS1. As illustrated in FIG. 24, in the case where a plane at the same height as that of the detection unit 32 is set as the reference surface RS1, a height between the reference surface RS1 and the second surface 12*b* becomes the reference surface height RH1. The reference surface height detection unit (not illustrated) of the integrated control unit 46 (see FIG. 1) detects the reference surface height RH1 on the basis of a detection result obtained by the detection unit 32 detecting the reflection light LB reflected by the second surface 12*b* according to the incidence of the laser light LA on the first surface 12*a* of the non-formation region RA (see FIG. 4) of the mold 12 from the incidence unit 30.

Further, in the case where the plane at the same height as that of the detection unit 32 is set as the reference surface RS1, the height between the reference surface RS1 and the drug surface 16*a* (the plurality of positions T) becomes the height Hb1 corresponding to the first height of the present invention. The first height detection unit 61 (see FIG. 7) detects the height Hb1 of each needle-shaped recess 14 on the basis of the detection result obtained by the detection unit 32 detecting the reflection light LB reflected by the drug surface 16*a* (the plurality of positions T) according to the incidence of the laser light LA on the drug surface 16*a* (the plurality of positions T) in the needle-shaped recesses 14 of the mold 12 from the incidence unit 30. It is possible to detect the height Hb1 in one measurement without performing the measurement of the height of the first surface 12*a*, unlike the case where the first surface 12*a* is set as the reference surface as in each of the above embodiment.

The second height detection unit 62 subtracts the height Hb1 with respect to the reference surface height RH1 from the reference surface height RH1 and the height Hb1 of each needle-shaped recess 14 to detect the height Ht of the drug surface 16*a* (the plurality of positions T) in each needle-shaped recess 14.

Figure 25:
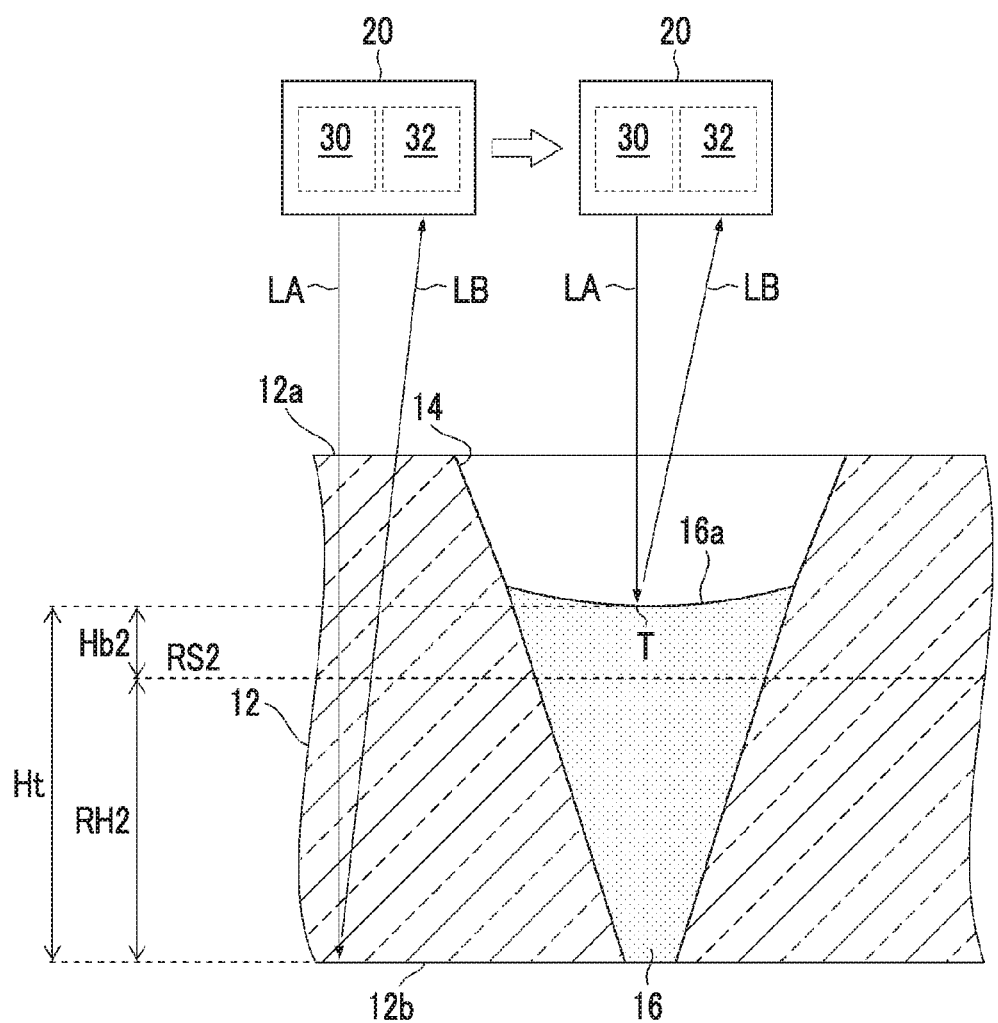
FIG. 25 is an illustrative diagram illustrating a process of detecting the height Ht in a case where an arbitrary plane between the first surface and the second surface of the mold is set as a reference surface.

FIG. 25 is a diagram illustrating a process of detecting the height Ht in a case where an arbitrary plane between the first surface 12*a* and the second surface 12*b* of the mold 12 is set as the reference surface RS2. As illustrated in FIG. 25, in a case where the reference surface RS2 is set between the first surface 12*a* and the second surface 12*b*, the height between the reference surface RS2 and the second surface 12*b* becomes the reference surface height RH2, and the height between the reference surface RS2 and the drug surface 16*a* (the plurality of positions T) becomes the height Hb2 corresponding to the first height of the present invention. In this case, it is possible to detect the height Ht of the drug surface 16*a* (the plurality of positions T) in the needle-shaped recess 14 from the reference surface height RH2 and the height Hb2 of each needle-shaped recess 14.

Since processes after the detection of the height Ht are basically the same as in the first embodiment, specific description thereof will be omitted herein. For the reference surface heights RH1 and RH2, a height measured in advance is stored in the storage unit 47 or the like, and the reference surface heights RH1 and RH2 may be able to be acquired from the storage unit 47 or the like, similar to the thickness information 64 illustrated in FIG. 7 or the like described above.

In each of the above embodiments, the reflection light LB reflected by the drug surface 16*a* in each needle-shaped recess 14 due to the incidence of the laser light LA from the first surface 12*a* of the mold 12 by the incidence unit 30 is detected by the detection unit 32, but the present invention is not limited thereto. For example, transmitted light emitted from the drug surface 16*a* in each needle-shaped recess 14 due to the incidence of the laser light LA from the second surface 12*b* side of the mold 12 by the incidence unit 30 is detected by the detection unit 32, and the heights Hb and Ht of the drug surface 16*a* of each needle-shaped recess 14 may be obtained on the basis of a result of the detection (the first detection result of the present invention).

Although the laser light LA has been described as an example of the measurement wave of the present invention in each of the above embodiments, various physical waves such as heat, radio waves, and sound waves other than light such as the laser light LA may be used as the measurement wave of the present invention.

[Program Causing Computer to Function as Means for Measuring Volume of Drug]

A program (the above-described measurement program 51 or the like) for causing a computer to function as a measurement device described in each of the above embodiments can be recorded on a compact disc read only memory (CD-ROM), a magnetic disk, or another computer-readable medium (a tangible non-transitory information storage medium), and the program can be provided through the information storage medium. A program signal can be provided as a download service using a communication network such as the Internet, instead of an aspect in which the program is stored in such an information storage medium and provided.

EXPLANATION OF REFERENCES

- 10: measurement device
- 12: mold
- 12a: first face
- 12b: second surface
- 14: needle-shaped recess
- 16: drug
- 16a: drug surface
- 20: laser displacement meter
- 21: device body
- 30: incidence unit
- 32: detection unit
- 40: imaging element
- 51: measurement program
- 59: laser displacement meter control unit
- 60: thickness acquisition unit
- 61: first height detection unit
- 62: second height detection unit
- 63: volume calculation unit

What is claimed is:

1. A measurement method of measuring a volume of a drug filled in a needle-shaped recess of a mold in which a plurality of needle-shaped recesses that are inverted types of a micro-needle are formed, the measurement method comprising:
    a reference surface height acquisition step of acquiring a reference surface height that is a height between a reference surface determined in advance with respect to a first surface on the side on which the drug is filled in the mold or a second surface opposite to the first surface, and the second surface;
    a detection result acquisition step of acquiring a first detection result obtained by detecting, for each needle-shaped recess, a measurement wave emitted from a drug surface that is a surface of the drug according to incidence of the measurement wave on the drug in the needle-shaped recess;
    a first height detection step of detecting, for each needle-shaped recess, a first height between the reference surface and the drug surface on the basis of the first detection result acquired in the detection result acquisition step;
    a second height detection step of detecting, for each needle-shaped recess, a second height from the second surface to the drug surface, from the reference surface height acquired in the reference surface height acquisition step and the first height of each needle-shaped recess detected in the first height detection step; and
    a volume calculation step of calculating, for each needle-shaped recess, the volume of the drug in the needle-shaped recess on the basis of the second height of each needle-shaped recess detected in the second height detection step and a known shape of the needle-shaped recess.

2. The measurement method according to claim 1, wherein the volume calculation step includes calculating a total volume of the drug filled in the mold from the volume of the drug of each needle-shaped recess.

3. The measurement method according to claim 1, wherein the detection result acquisition step includes acquiring, for each needle-shaped recess, the first detection result obtained by detecting the measurement wave emitted from the plurality of positions according to the incidence of the measurement wave on the plurality of positions of the drug surface,
    the first height detection step includes detecting, for each needle-shaped recess, the first height from the plurality of positions to the reference surface on the basis of the first detection result of each needle-shaped recess acquired in the detection result acquisition step,
    the second height detection step includes detecting for each needle-shaped recess, the second height from the second surface to each of the plurality of positions from the reference surface height and the first height of the plurality of positions of each needle-shaped recess detected in the first height detection step, and
    the volume calculation step includes calculating the volume of the drug in the needle-shaped recess for each needle-shaped recess on the basis of the second height of the plurality of positions of each needle-shaped recess detected in the second height detection step and the known shape of the needle-shaped recess.

4. The measurement method according to claim 3, wherein the detection result acquisition step includes acquiring the first detection result obtained by a plurality of detection units detecting the measurement wave emitted in different directions from the plurality of positions according to incidence of the measurement wave on the plurality of positions of each needle-shaped recess from the plurality of incidence units,
    the first height detection step includes performing the detection of the first height of the plurality of positions for each needle-shaped recess in each detection unit on the basis of the first detection result of each detection unit acquired in the detection result acquisition step,
    the second height detection step includes performing the detection of the second height of the plurality of positions for each needle-shaped recess in each detection unit, on the basis of the first height of the plurality of positions of each detection unit detected in the first height detection step, and the reference surface height, and
    the volume calculation step includes integrating, for each the needle-shaped recess, the second height of the plurality of positions of each detection unit detected in the second height detection step, and calculating the volume of the drug in the needle-shaped recess for each needle-shaped recess on the basis of the second integrated height of the plurality of positions of each needle-shaped recess and the known shape of the needle-shaped recess.

5. The measurement method according to claim 3, wherein the detection result acquisition step includes performing incidence of the measurement wave at an incidence angle determined in advance for every plurality of positions on the plurality of positions from the incidence unit while relatively moving the mold and the incidence unit that causes the measurement wave to be incident on the drug surface in a direction parallel to the first surface, and detecting the measurement wave emitted from each of the plurality of positions according to the incidence of the measurement wave using the detection unit to acquire the first detection result.

6. The measurement method according to claim 3, wherein the detection result acquisition step includes performing incidence of the measurement wave on the plurality of positions from the incidence unit while relatively moving the mold and the incidence unit that causes the measurement wave to be incident on the drug surface in a direction parallel to the first surface, and detecting the measurement wave emitted in a direction determined in advance for every plurality of positions from the plurality of positions according to the incidence of the measurement wave using the detection unit to acquire the first detection result.

7. The measurement method according to claim 3, wherein the detection result acquisition step includes performing scan for causing the measurement wave to he incident on the plurality of positions from the incidence unit a plurality of times while relatively moving the mold and the incidence unit that causes the measurement wave to be incident on the drug surface in a direction parallel to the first surface, and detecting, for each scan, the measurement wave emitted in a different direction from the plurality of positions for each scan using the detection unit to acquire the first detection result,
the first height detection step includes performing, for each scan, detection of the first height of the plurality of positions of each needle-shaped recess on the basis of the first detection result for each scan acquired in the detection result acquisition step,
the second height detection step includes performing, for each scan, the detection of the second height of the plurality of positions for each needle-shaped recess on the basis of the first height of the plurality of positions for each scan detected in the first height detection step, and the reference surface height, and
the volume calculation step includes integrating, for each the needle-shaped recess, the second height of the plurality of positions of each scan detected in the second height detection step, and calculating the volume of the drug in the needle-shaped recess for each needle-shaped recess on the basis of the second integrated height of the plurality of positions of each needle-shaped recess and the known shape of the needle-shaped recess.

8. The measurement method according to claim 1, wherein the detection result acquisition step starts within a predetermined time after the drug is filled in the needle-shaped recesses of the mold or at a certain time within the predetermined time.

9. The measurement method according to claim 1, wherein the volume of the drug decreases over time due to evaporation of water contained in the drug,
the measurement method further comprises
an elapsed time acquisition step of acquiring an elapsed time until the detection result acquisition step starts after the drug is filled in the needle-shaped recess of the mold; and
a correction value acquisition step of acquiring a correction value for correcting a decrease over time in the volume of the drug filled in the needle-shaped recess, and
the volume calculation step includes correcting the volume of the drug in the needle-shaped recess with the correction value acquired in the correction value acquisition step on the basis of the elapsed time acquired in the elapsed time acquisition step, and calculating the amount of filling of the drug filled in the needle-shaped recess for each needle-shaped recess.

10. The measurement device according to claim 1, further comprising:
a first incidence step of causing the measurement wave to be incident on the drug surface in each needle-shaped recess; and
a first detection step of detecting, for each needle-shaped recess, the measurement wave emitted from the drug surface according to the incidence of the measurement wave in the first incidence step,
wherein the detection result acquisition step includes acquiring the first detection result of the measurement wave detected in the first detection step.

11. The measurement method according to claim 1, wherein the reference surface height acquisition step includes acquiring the reference surface height from the storage unit that stores the reference surface height in advance.

12. The measurement method according to claim 1, wherein the reference surface is the first surface, and the reference surface height is a thickness of the mold,
the reference surface height acquisition step includes acquiring a second detection result obtained by detecting the measurement wave emitted from the first surface and the second surface according to incidence of the measurement wave on the non-formation region of the needle-shaped recess included in the mold, and acquiring the thickness of the mold as the reference surface height on the basis of the second detection result.

13. The measurement method according to claim 12, further comprising:
a second incidence step of causing the measurement wave to be incident on the non-formation region of the mold; and
a second detection step of detecting the measurement wave emitted from the first surface and the second surface of the non-formation region according to the incidence of the measurement wave in the second incidence step,
wherein the reference surface height acquisition step includes acquiring the second detection result of the measurement wave detected in the second detection step.

14. The measurement method according to claim 13, wherein the second incidence step includes causing the measurement wave to be incident on the first surface of the non-formation region, and
the second detection step includes detecting the measurement wave emitted from the first surface due to reflection at the first surface according to the incidence of the measurement wave in the second incidence step, and the measurement wave incident on the mold from the first surface and emitted from the second surface due to reflection at the second surface of the non-formation region.

15. The measurement method according to claim 1, wherein the reference surface is a plane that is at the same height as that of the detection unit that detects the measurement wave emitted from the drug surface.

16. The measurement method according to claim 1, further comprising:
adding a dye to the drug that is filled in the needle-shaped recess.

17. The measurement method according to claim 1, further comprising
performing hydrophilic treatment on the first surface before filling of the drug in the needle-shaped recess.

18. A measurement device that measures a volume of a drug filled in a needle-shaped recess of a mold in which a plurality of needle-shaped recesses that are inverted types of a micro-needle are formed, the measurement device comprising:
a reference surface height acquisition unit that acquires a reference surface height that is a height between a reference surface determined in advance with respect to a first surface on the side on which the drug is filled in the mold or a second surface opposite to the first surface, and the second surface;
a detection result acquisition unit that acquires a first detection result obtained by detecting, for each needle-shaped recess, a measurement wave emitted from a drug surface that is a surface of the drug according to incidence of the measurement wave on the drug in the needle-shaped recess;
a first height detection unit that detects, for each needle-shaped recess, a first height between the reference surface and the drug surface on the basis of the first detection result acquired by the detection result acquisition unit;
a second height detection unit that detects, for each needle-shaped recess, a second height from the second surface to the drug surface from the reference surface height acquired by the reference surface height acquisition unit and the first height of each needle-shaped recess detected by the first height detection unit; and
a volume calculation unit that calculates, for each needle-shaped recess, the volume of the drug in the needle-shaped recess on the basis of the second height of each needle-shaped recess detected by the second height detection unit and a known shape of the needle-shaped recess.

19. The measurement device according to claim 18, further comprising:
a first incidence unit that causes the measurement wave to be incident on the drug in the needle-shaped recess, for each needle-shaped recess; and
a first detection unit that detects, for each needle-shaped recess, the measurement wave emitted from the drug surface according to the incidence of the measurement wave by the first incidence unit,
wherein the detection result acquisition unit acquires the first detection result of the measurement wave detected by the first detection unit.

20. The measurement device according to claim 18,
wherein the reference surface is the first surface, and the reference surface height is a thickness of the mold,
the measurement device includes
a second incidence unit that causes the measurement wave to be incident on a non-formation region of the needle-shaped recess included in the mold; and
a second detection unit that detects the measurement wave emitted front the first surface and the second surface of the non-formation region according to the incidence of the measurement wave by the second incidence unit, and
the reference surface height acquisition unit acquires the second detection result of the measurement wave detected by the second detection unit, and acquires the thickness of the mold as the reference surface height on the basis of the second detection result.

21. The measurement device according to claim 18,
wherein the reference surface height acquisition unit acquires the reference surface height from the storage unit that stores the reference surface height in advance.

22. A non-transitory computer-readable tangible medium recording a program that causes a computer to function as means for measuring a volume of a drug filled in a needle-shaped recess of a mold in which a plurality of needle-shaped recesses that are inverted types of a micro-needle are formed, the program causing the computer to function as:
a reference surface height acquisition unit that acquires a reference surface height that is a height between a reference surface determined in advance with respect to a first surface on the side on which the drug is filled in the mold or a second surface opposite to the first surface, and the second surface;
a detection result acquisition unit that acquires a first detection result obtained by detecting, for each needle-shaped recess, a measurement wave emitted from a drug surface that is a surface of the drug according to incidence of the measurement wave on the drug in the needle-shaped recess;
a first height detection unit that detects, for each needle-shaped recess, a first height between the reference surface and the drug surface on the basis of the first detection result acquired by the detection result acquisition unit;
a second height detection unit that detects, for each needle-shaped recess, a second height from the second surface to the drug surface from the reference surface height acquired by the reference surface height acquisition unit and the first height of each needle-shaped recess detected by the first height detection unit; and
a volume calculation unit that calculates, for each needle-shaped recess, the volume of the drug in the needle-shaped recess on the basis of the second height of each needle-shaped recess detected by the second height detection unit and a known shape of the needle-shaped recess.

* * * * *